US006358716B1

(12) United States Patent
Bulthuis et al.

(10) Patent No.: US 6,358,716 B1
(45) Date of Patent: Mar. 19, 2002

(54) METHOD FOR THE PRODUCTION OF GLYCEROL BY RECOMBINANT ORGANISMS

(75) Inventors: Ben A. Bulthuis, Leiden (NL); Anthony Arthur Gatenby, Wilmington, DE (US); Sharon Loretta Haynie, Philadelphia, PA (US); Amy Kuang-Hua Hsu, Redwood City; Richard D. Lareau, Mountain View, both of CA (US)

(73) Assignee: E. I. du Ponte de Nemours and Company, Wilmington, DE (US)

( * ) Notice: Subject to any disclaimer, the term of this patent is extended or adjusted under 35 U.S.C. 154(b) by 0 days.

(21) Appl. No.: 09/297,928

(22) PCT Filed: Nov. 10, 1997

(86) PCT No.: PCT/US97/20293

§ 371 Date: May 11, 1999

§ 102(e) Date: May 11, 1999

(87) PCT Pub. No.: WO98/21340

PCT Pub. Date: May 22, 1998

Related U.S. Application Data

(60) Provisional application No. 60/030,602, filed on Nov. 13, 1996.

(51) Int. Cl.[7] ................................................. C12P 7/20
(52) U.S. Cl. ........................................................ 435/159
(58) Field of Search ............................. 435/159, 252.33

(56) References Cited

FOREIGN PATENT DOCUMENTS

| WO | WO96 35795 | 11/1996 |
|----|------------|---------|
| WO | WO96 35796 | 11/1996 |
| WO | WO96 35799 | 11/1996 |
| WO | WO96 41888 | 12/1996 |
| WO | WO 97 07199 A1 | 2/1997 |
| WO | WO98 21339 | 5/1998 |
| WO | WO98 21341 | 5/1998 |

OTHER PUBLICATIONS

Nevoigt et al. Reduced Pyruvate Decarboxylase and Increased Glycerol–3–Phosphate Dehydrongenase [NAD+] Levels Enhance GLycerol Production in *Saccharomyces cerevisiae*. Yeast (1996) 12:1331–1337, Oct. 1996.*

Jones et al. Current trends in molecular recognition and bioseparation. J. of Chromatography (1995) 707:3–22, Jul. 1995.*

Ben–Amotz et al., Experientia, 38, 49–52, 1982.

Albertyn et al., Mol. Cell. Biol., 14, 4135–4144, 1994.

Wang et al., J. Bact., 176, 7091–7095, 1994.

Hirayama et al., "Cloning and characterization of seven cDNAs for hyperosmolarity–responsive (HOR) genes of Saccharomyces", *Mol. Gen. Genet*, 249, 127–128, 1995.

Omori et al., Breeding of High Glycerol–Producing Shochu Yeast (*Saccharomyces cerevisiae*) with Acquired Salt Tolerance, *Jounral of Fermentation and Bioengineering*, 79, 560–565, 1995.

Larason et al., Mol. Microbiol., 10, 1101, 1993.

Norbeck et al., J. Biol. Chem., 271, 13875, 1996.

Eustace, Rosanne et al., Selective hybridization of wine yeast for higher yields of glycerol, Can. J. Microbiol., 1987, pp. 112–117, 33.

* cited by examiner

*Primary Examiner*—Ponnathapu Achutamurthy
*Assistant Examiner*—Kathleen Kerr

(57) ABSTRACT

Recombinant organisms are provided comprising genes encoding a glycerol-3-phosphate dehydrogenase and/or a glycerol-3-phosphatase activity useful for the production of glycerol from a variety of carbon substrates.

6 Claims, No Drawings

METHOD FOR THE PRODUCTION OF GLYCEROL BY RECOMBINANT ORGANISMS

This application is a national filing of PCT/US97/20293, filed internationally Nov. 10, 1997, which in turn claims benefit of US Provisional application 60/030,602, filed Nov. 13, 1996.

FIELD OF INVENTION

The present invention relates to the field of molecular biology and the use of recombinant organisms for the production of desired compounds. More specifically it describes the expression of cloned genes for glycerol-3-phosphate dehydrogenase (G3PDH) and glycerol-3-phosphatase (G3P phosphatase), either separately or together, for the enhanced production of glycerol.

BACKGROUND

Glycerol is a compound in great demand by industry for use in cosmetics, liquid soaps, food, pharmaceuticals, lubricants, anti-freeze solutions, and in numerous other applications. The esters of glycerol are important in the fat and oil industry.

Not all organisms have a natural capacity to synthesize glycerol. However, the biological production of glycerol is known for some species of bacteria, algae, and yeasts. The bacteria *Bacillus licheniformis* and *Lactobacillus lycopersica* synthesize glycerol. Glycerol production is found in the halotolerant algae Dunaliella sp. and *Asteronmonas gracilis* for protection against high external salt concentrations (Ben-Amotz et al., (1982) *Experientia* 38:49–52). Similarly, various osmotolerant yeasts synthesize glycerol as a protective measure. Most strains of Saccharomyces produce some glycerol during alcoholic fermentation, and this can be increased physiologically by the application of osmotic stress (Albertyn et al., (1994) *Mol. Cell. Biol.* 14, 4135–4144). Earlier this century glycerol was produced commercially with Saccharomyces cultures to which steering reagents were added such as sulfites or alkalis. Through the formation of an inactive complex, the steering agents block or inhibit the conversion of acetaldehyde to ethanol, thus, excess reducing equivalents (NADH) are available to or "steered" towards dihydroxyacetone phosphate (DHAP) for reduction to produce glycerol. This method is limited by the partial inhibition of yeast growth that is due to the sulfites. This limitation can be partially overcome by the use of alkalis which create excess NADH equivalents by a different mechanism. In this practice, the alkalis initiated a Cannizarro disproportionation to yield ethanol and acetic acid from two equivalents of acetaldehyde.

The gene encoding glycerol-3-phosphate dehydrogenase (DAR1,GPD1) has been cloned and sequenced from *Sacchatromyces diastaticus* (Wang et al., (1994). *J. Bact.* 176:7091–7095). The DAR1 gene was cloned into a shuttle vector and used to transform *E. coli* where expression produced active enzyme. Wang et al., supra recognizes that DAR1 is regulated by the cellular osmotic environment but does not suggest how the gene might be used to enhance glycerol production in a recombinant organism.

Other glycerol-3-phosphate dehydrogenase enzymes have been isolated. For example, sn-glycerol-3-phosphate dehydrogenase has been cloned and sequenced from *S. cerevisiae* (Larason et al., (1993) *Mol. Microbiol.*, 10:1101, (1993)). Albertyn et al., (1994) *Mol. Cell. Biol.*, 14:4135) teach the cloning of GPD1 encoding a glycerol-3-phosphate dehydrogenase from *S. cerevisiae*. Like Wang et al., both Albertyn et al., and Larason et al. recognize the osmo-sensitivity of the regulation of this gene but do not suggest how the gene might be used in the production of glycerol in a recombinant organism.

As with G3DPH, glycerol-3-phosphatase has been isolated from *Saccharomyces cerevisiae* and the protein identified as being encoded by the GPP1 and GPP2 genes (Norbeck et al., (1996) *J. Biol. Chem.*, 271:13875). Like the genes encoding G3DPH, it appears that GPP2 is osmotically-induced.

There is no known art that teaches glycerol production from recombinant organisms with G3PDH/G3P phosphatase expressed together or separately. Nor is there known art that teaches glycerol production from any wild-type organism with these two enzyme activities that does not require applying some stress (salt or an osmolyte) to the cell. Eustace ((1987), *Can. J. Microbiol.*, 33:112–117)) teaches away from achieving glycerol production by recombinant DNA techniques. By selective breeding techniques, these investigators created a hybridized yeast strain that produced glycerol at greater levels than the parent strains: however, the G3PDH activity remained constant or slightly lower.

A microorganism capable of producing glycerol under physiological conditions is industrially desirable, especially when the glycerol itself will be used as a substrate in vivo as part of a more complex catabolic or biosynthetic pathway that could be perturbed by osmotic stress or the addition of steering agents.

The problem to be solved, therefore, is how to direct carbon flux towards glycerol production by the addition or enhancement of certain enzyme activities, especially G3PDH and G3P phosphatase which respectively catalyze the conversion of dihydroxyacetone phosphate (DHAP) to glycerol-3-phosphate (G3P) and then to glycerol. This process has not previously been described for a recombinant organism and required the isolation of genes encoding the two enzymes and their subsequent expression. A surprising and unanticipated difficulty encountered was the toxicity of G3P phosphatase to the host which required careful control of its expression levels to avoid growth inhibition.

SUMMARY OF THE INVENTION

The present invention provides a method for the production of glycerol from a recombinant organism comprising: (i) transforming a suitable host cell with an expression cassette comprising either or both
  (a) a gene encoding a glycerol-3-phosphate dehydrogenase enzyme;
  (b) a gene encoding a glycerol-3-phosphate phosphatase enzyme: (ii) culturing the transformed host cell in the presence of at least one carbon source selected from the group consisting of monosaccharides, oligosaccharides. polysaccharides, and single-carbon substrates, or mixtures thereof whereby glycerol is produced; and (iii) recovering the glycerol. Glucose is the most preferred carbon source.

The invention further provides transformed host cells comprising expression cassettes capable of expressing glycerol-3-phosphate dehydrogenase and glycerol-3-phosphatase activities for the production of glycerol.

BRIEF DESCRIPTION OF BIOLOGICAL DEPOSITS AND SEQUENCE LISTING

Applicants have made the following biological deposits under the terms of the Budapest Treaty on the International Recognition of the Deposit of Micro-organisms for the Purposes of Patent Procedure:

| Depositor Identification Reference | Int'l. Depository Designation | Date of Deposit |
|---|---|---|
| *Escherichia coli* pAH21/DH5α (containing the GPP2 gene) | ATCC 98187 | 26 September 1996 |
| *Escherichia coli* (pDAR1A/AA200) (containing the DAR1 gene) | ATCC 98248 | 6 November 1996 |

"ATCC" refers to the American Type Culture Collection international depository located at 12301 Parklawn Drive Rockville, Md. 20852 U.S.A. The designation is the accession number of the deposited material.

Applicants have provided 23 sequences in conformity with the Rules for the Standard Representation of Nucleotide and Amino Acid Sequences in Patent Applications (Annexes I and II to the Decision of the President of the EPO, published in Supplement No. 2 to OJ EPO. 12/1992) and with 37 C.F.R. 1.821–1.825 and Appendices A and B (Requirements for Application Disclosures Containing Nucleotides and/or Amino Acid Sequences).

DETAILED DESCRIPTION OF THE INVENTION

The present invention provides a method for the biological production of glycerol from a fermentable carbon source in a recombinant organism. The method provides a rapid inexpensive and environmentally-responsible source of glycerol useful in the cosmetics and pharmaceutical industries. The method uses a microorganism containing cloned homologous or heterologous genes encoding glycerol-3-phosphate dehydrogenase (G3PDH) and/or glycerol-3-phosphatase (G3P phosphatase). The microorganism is contacted with a carbon source and glycerol is isolated from the conditioned media. The genes may be incorporated into the host microorganism separately or together for the production of glycerol.

As used herein the following terms may be used for interpretation of the claims and specification.

The terms "glycerol-3-phosphate dehydrogenase" and "G3PDH" refer to a polypeptide responsible for an enzyme activity that catalyzes the conversion of dihydroxyacetone phosphate (DHAP) to glycerol-3-phosphate (G3P). In vivo G3PDH may be NADH, NADPH; or FAD-dependent. The NADH-dependent enzyme (EC 1.1.1.8) is encoded by several genes including GPD1 (GenBank Z74071×2), or GPD2 (GenBank Z35169×1), or GPD3 (GenBank G984182), or DAR1 (GenBank Z74071×2). The NADPH-dependent enzyme (EC 1.1.1.94) is encoded by gpsA (GenBank U321643, (cds 197911–196892) G466746 and L45246). The FAD-dependent enzyme (EC 1.1.99.5) is encoded by GUT2 (GenBank Z47047×23), or glpD (GenBank G147838), or glpABC (GenBank M20938).

The terms "glycerol-3-phosphate phosphatase", "sn-glycerol-3-phosphatase", or "d,l-glycerol phosphatase", and "G3P phosphatase" refer to a polypeptide responsible for an enzyme activity that catalyzes the conversion of glycerol-3-phosphate to glycerol. G3P phosphatase is encoded by GPP1 (GenBank Z47047×125), or GPP2 (GenBank U18813×11).

The term "glycerol kinase" refers to a polypeptide responsible for an enzyme activity that catalyzes the conversion of glycerol to glycerol-3-phosphate, or glycerol-3-phosphate to glycerol, depending on reaction conditions. Glycerol kinase is encoded by GUT1 (GenBank U11583×9).

The terms "GPD1", "DAR1", "OSG1", "D2830" and "YDL022W" will be used interchangeably and refer to a gene that encodes a cytosolic glycerol-3-phosphate dehydrogenase and is characterized by the base sequence given as SEQ ID NO:1.

The term "GPD2" refers to a gene that encodes a cytosolic glycerol-3-phosphate dehydrogenase and is characterized by the base sequence given in SEQ ID NO:2.

The terms "GUT2" and "YIL155C" are used interchangeably and refer to a gene that encodes a mitochondrial glycerol-3-phosphate dehydrogenase and is characterized by the base sequence given in SEQ ID NO:3.

The terms "GPP1", "RHR2" and "YIL053W" are used interchangeably and refer to a gene that encodes a cytosolic glycerol-3-phosphatase and is characterized by the base sequence given in SEQ ID NO:4.

The terms "GPP2", "HOR2" and "YER062C" are used interchangeably and refer to a gene that encodes a cytosolic glycerol-3-phosphatase and is characterized by the base sequence given as SEQ ID NO:5.

The term "GUT1" refers to a gene that encodes a cytosolic glycerol kinase and is characterized by the base sequence given as SEQ ID NO:6.

As used herein, the terms "function" and "enzyme function" refer to the catalytic activity of an enzyme in altering the energy required to perform a specific chemical reaction. Such an activity may apply to a reaction in equilibrium where the production of both product and substrate may be accomplished under suitable conditions.

The terms "polypeptide" and "protein" are used herein interchangeably.

The terms "carbon substrate" and "carbon source" refer to a carbon source capable of being metabolized by host organisms of the present invention and particularly mean carbon sources selected from the group consisting of monosaccharides, oligosaccharides, polysaccharides, and one-carbon substrates or mixtures thereof.

The terms "host cell" and "host organism" refer to a microorganism capable of receiving foreign or heterologous genes and expressing those genes to produce an active gene product.

The terms "foreign gene", "foreign DNA", "heterologous gene", and "heterologous DNA" all refer to genetic material native to one organism that has been placed within a different host organism.

The terms "recombinant organism" and "transformed host" refer to any organism transformed with heterologous or foreign genes. The recombinant organisms of the present invention express foreign genes encoding G3PDH and G3P phosphatase for the production of glycerol from suitable carbon substrates.

"Gene" refers to a nucleic acid fragment that expresses a specific protein, including regulatory sequences preceding (5' non-coding) and following (3' non-coding) the coding region. The terms "native" and "wild-type" gene refer to the gene as found in nature with its own regulatory sequences.

As used herein, the terms "encoding" and "coding" refer to the process by which a gene, through the mechanisms of transcription and translation, produces an amino acid sequence. The process of encoding a specific amino acid sequence is meant to include DNA sequences that may involve base changes that do not cause a change in the encoded amino acid, or which involve base changes which may alter one or more amino acids, but do not affect the functional properties of the protein encoded by the DNA sequence. Therefore, the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alterations in the gene sequence which reflect the degeneracy of the genetic code, or which result in the production of a chemically equivalent amino acid at a given site, are contemplated: thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity in the encoded products. Moreover, the skilled artisan recognizes that sequences encompassed by this invention are also defined by their ability to hybridize, under stringent conditions (0.1×SSC, 0.1% SDS, 65° C.), with the sequences exemplified herein.

The term "expression" refers to the transcription and translation to gene product from a gene coding for the sequence of the gene product.

The terms "plasmid", "vector", and "cassette" as used herein refer to an extra chromosomal element often carrying genes which are not part of the central metabolism of the cell and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The terms "transformation" and "transfection" refer to the acquisition of new genes in a cell after the incorporation of nucleic acid. The acquired genes may be integrated into chromosomal DNA or introduced as extrachromosomal replicating sequences. The term "transformant" refers to the cell resulting from a transformation.

The term "genetically altered" refers to the process of changing hereditary material by transformation or mutation.

Representative Enzyme Pathway

It is contemplated that glycerol may be produced in recombinant organisms by the manipulation of the glycerol biosynthetic pathway found in most microorganisms. Typically, a carbon substrate such as glucose is converted to glucose-6-phosphate via hexokinase in the presence of ATP. Glucose-phosphate isomerase catalyzes the conversion of glucose-6-phosphate to fructose-6-phosphate and then to fructose-1,6-diphosphate through the action of 6-phosphofructokinase. The diphosphate is then taken to dihydroxyacetone phosphate (DHAP) via aldolase. Finally NADH-dependent G3PDH converts DHAP to glycerol-3-phosphate which is then dephosphorylated to glycerol by G3P phosphatase. (Agarwal (1990), *Adv. Biochem. Engrg.* 41:114).

Alternate Pathways for Glycerol Production

An alternative pathway for glycerol production from DHAP has been suggested (Wang et al., (1994) *J. Bact.* 176:7091–7095). In this proposed pathway DHAP could be dephosphorylated by a specific or non-specific phosphatase to give dihydroxyacetone, which could then be reduced to glycerol by a dihydroxy-acetone reductase. Dihydroxyacetone reductase is known in prokaryotes and in *Schizosaccharomyces pombe*, and cloning and expression of such activities together with an appropriate phosphatase could lead to glycerol production. Another alternative pathway for glycerol production from DHAP has been suggested (Redkar (1995), *Experimental Mycology*, 19:241, 1995). In this pathway DHAP is isomerized to glyceraldehyde-3-phosphate by the common glycolytic enzyme triose phosphate isomerase. Glyceraldehyde-3-phosphate is dephosphorylated to glyceraldehyde, which is then reduced by alcohol dehydrogenase or a NADP-dependent glycerol dehydrogenase activity. The cloning and expression of the phosphatase and dehydrogenase activities from *Aspergillus nidulans* could lead to glycerol production.

Genes Encoding G3PDH and G3P Phosphatase

The present invention provides genes suitable for the expression of G3PDH and G3P phosphatase activities in a host cell.

Genes encoding G3PDH are known. For example, GPD1 has been isolated from Saccharomyces and has the base sequence given by SEQ ID NO:1. encoding the amino acid sequence given in SEQ ID NO:7 (Wang et al., supra). Similarly, G3PDH activity has also been isolated from Saccharomyces encoded by GPD2 having the base sequence given in SEQ ID NO:2 encoding the amino acid sequence given in SEQ ID NO:8 (Eriksson et al., (1995) *Mol. Microbiol.*, 17:95).

For the purposes of the present invention it is contemplated that any gene encoding a polypeptide responsible for G3PDH activity is suitable wherein that activity is capable of catalyzing the conversion of dihydroxyacetone phosphate (DHAP) to glycerol-3-phosphate (G3P). Further, it is contemplated that any gene encoding the amino acid sequence of G3PDH as given by SEQ ID NOS:7, 8, 9, 10, 11 and 12 corresponding to the genes GPD1, GPD2, GUT2, gpsA, glpD, and the α subunit of glpABC respectively, will be functional in the present invention wherein that amino acid sequence may encompass amino acid substitutions, deletions or additions that do not alter the function of the enzyme. The skilled person will appreciate that genes encoding G3PDH isolated from other sources will also be suitable for use in the present invention. For example, genes isolated from prokaryotes include GenBank accessions M34393, M20938, L06231, U12567, L45246, L45323, L45324, L45325, U32164, U32689, and U39682. Genes isolated from fungi include GenBank accessions U30625, U30876 and X56162; genes isolated from insects include GenBank accessions X61223 and X14179; and genes isolated from mammalian sources include GenBank accessions U12424, M25558 and X78593.

Genes encoding G3P phosphatase are known. For example, GPP2 has been isolated from *Saccharomyces cerevisiae* and has the base sequence given by SEQ ID NO:5, which encodes the amino acid sequence (given in SEQ ID NO:13 (Norbeck et al., (1996), *J. Biol. Chem.*, 271:13875).

For the purposes of the present invention, any gene encoding a G3P phosphatase activity is suitable for use in the method wherein that activity is capable of catalyzing the conversion of glycerol-3-phosphate to glycerol. Further, any gene encoding the amino acid sequence of G3P phosphatase as given by SEQ ID NOS:13 and 14 corresponding to the genes GPP2 and GPP1 respectively, will be functional in the present invention including any amino acid sequence that encompasses amino acid substitutions, deletions or additions that do not alter the function of the G3P phosphatase enzyme. The skilled person will appreciate that genes encoding G3P phosphatase isolated from other sources will also be suitable for use in the present invention. For example, the dephosphorylation of glycerol-3-phosphate to yield glycerol may be achieved with one or more of the following general or specific phosphatases: alkaline phosphatase (EC 3.1.3.1) [GenBank M19159, M29663, U02550 or M339651]; acid phosphatase (EC 3.1.3.2) [GenBank U51210, U19789, U28658 or L205661]; glycerol-3-phosphatase (E.C. 3.1.3.21) [GenBank Z38060 or U18813x11]; glucose-1-phosphatase (EC 3.1.3.10) [GenBank M338071]; glucose-6-phosphatase (EC 3.1.3.9) [GenBank U00445]; fructose-1,6-bisphosphatase (EC 3.1.3.11) [GenBank X12545 or J03207] or phosphotidyl glycerol phosphate phosphatase (EC 3.1.3.27) [GenBank M23546 and M23628].

Genes encoding glycerol kinase are known. For example. GUT1 encoding the glycerol kinase from Saccharomyces has been isolated and sequenced (Pavlik et al. (1993), Curr. Genet., 24:21) and the base sequence is given by SEQ ID NO:6, which encodes the amino acid sequence given in SEQ ID NO:15. The skilled artisan will appreciate that, although glycerol kinase catalyzes the degradation of glycerol in nature, the same enzyme will be able to function in the synthesis of glycerol, converting glycerol-3-phosphate to glycerol under the appropriate reaction energy conditions. Evidence exists for glycerol production through a glycerol kinase. Under anaerobic or respiration-inhibited conditions, *Trypanosoma brucei* gives rise to glycerol in the presence of Glycerol-3-P and ADP. The reaction occurs in the glycosome compartment (Hammond, (1985), *J. Biol. Chem.*, 260:15646–15654).

Host Cells

Suitable host cells for the recombinant production of glycerol by the expression of G3PDH and G3P phosphatase may be either prokaryotic or eukaryotic and will be limited only by their ability to express active enzymes. Preferred host cells will be those bacteria, yeasts, and filamentous fungi typically useful for the production of glycerol such as Citriobacter, Enterobacter, Clostridium, Klebsiella, Aerobactet, Lactobacillus, Aspergillus, Saccharomyces, Schizosaccharomyces, Zygosaccharomyces, Pichia, Kluyveromyces. Candida, Hansenula, Debaryomyces. Mucor, Torulopsis, Methylobacter, Escherichia, Salmonella, Bacillus, Streptomyces and Pseudomnonas. Preferred in the present invention are *E*. coli and Saccharomyces.

Vectors and Expression Cassettes

The present invention provides a variety of vectors and transformation and expression cassettes suitable for the cloning, transformation and expression of G3PDH and G3P phosphatase into a suitable host cell. Suitable vectors will be those which are compatible with the bacterium employed. Suitable vectors can be derived, for example, from a bacteria, a virus (such as bacteriophage T7 or a M-13 derived phage), a cosmid, a yeast or a plant. Protocols for obtaining and using such vectors are known to those in the art (Sambrook et al., Molecular Cloning: A Laboratory Manual—volumes 1, 2, 3 (Cold Spring Harbor laboratory: Cold Spring Harbor, N.Y., 1989)).

Typically, the vector or cassette contains sequences directing transcription and translation of the appropriate gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell. Such control regions need not be derived from the genes native to the specific species chosen as a production host.

Initiation control regions or promoters, which are useful to drive expression of the G3PDH and G3P phosphatase genes in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, and TPI (useful for expression in Saccharomyces); AOX1 (useful for expression in Pichia); and lac, trp, $\lambda P_L$, $\lambda P_R$, T7, tac, and trc, (useful for expression in *E. coli*).

Termination control regions may also be derived from various genes native to the preferred hosts. Optionally, a termination site may be unnecessary; however, it is most preferred if included.

For effective expression of the instant enzymes, DNA encoding the enzymes are linked operably through initiation codons to selected expression control regions such that expression results in the formation of the appropriate messenger RNA.

Transformation of Suitable Hosts and Expression of G3PDH and G3P Phosphatase for the Production of Glycerol Once suitable cassettes are constructed they are used to transform appropriate host cells. Introduction of the cassette containing the genes encoding G3PDH and/or G3P phosphatase into the host cell may be accomplished by known procedures such as by transformation, e.g., using calcium-permeabilized cells, electroporation, or by transfection using a recombinant phage virus (Sambrook et al., supra).

In the present invention AH21 and DAR1 cassettes were used to transform the *E. coli* DH5α as fully described in the GENERAL METHODS and EXAMPLES.

Media and Carbon Substrates

Fermentation media in the present invention must contain suitable carbon substrates. Suitable substrates may include but are not limited to monosaccharides such as glucose and fructose, olioosaecharides such as lactose or sucrose, polysaccharides such as starch or cellulose or mixtures thereof and unpurified mixtures from renewable feedstocks such as cheese whey permeate, cornsteep liquors sugar beet molasses, and barley malt. Additionally, the carbon substrate may also be one-carbon substrates such as carbon dioxide, or methanol for which metabolic conversion into key biochemical intermediates has been demonstrated.

Glycerol production from single carbon sources (e.g., methanol, formaldehyde or formate) has been reported in methylotrophic yeasts (Yamada et al. (1989), *Agric. Biol. Chem.*, 53(2):541–543) and in bacteria (Hunter et al. (1985), *Biochemistry*, 24:4148–4155). These organisms can assimilate single carbon compounds, ranging in oxidation state from methane to formate, and produce glycerol. The pathway of carbon assimilation can be through ribulose monophosphate, through serine, or through xylulose-monophosphate (Gottschalk. *Bacterial Metabolism*, Second Edition, Springer-Verlag: New York (1986)). The ribulose monophosphate pathway involves the condensation of formate with ribulose-5-phosphate to form a 6 carbon sugar that becomes fructose and eventually the three carbon product. glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon-containing compounds such as methylamine, glucosamine and a variety of amino acids for metabolic activity. For example. methylotrophic yeast are known to utilize the carbon from methylamine to form trehalose or glycerol (Bellion et al. (1993), *Microb. Growth Cl Compd.*, [Int. Symp.], 7th, 415–32. Editor(s): Murrell, J. Collin; Kelly, Don P. Publisher: Intercept, Andover, UK). Similarly, various species of Candida will metabolize alanine or oleic acid (Sulter et al. (1990), *Arch. Microbiol.*, 153(5):485–9). Hence, the source of carbon utilized in the present invention may encompass a wide variety of carbon-containing substrates and will only be limited by the choice of organism.

Although all of the above mentioned carbon substrates and mixtures thereof are suitable in the present invention, preferred carbon substrates are monosaccharides, oligosaccharides, polysaccharides, single-carbon substrates or mixtures thereof. More preferred are sugars such as glucose, fructose, sucrose, maltose, lactose and single carbon substrates such as methanol and carbon dioxide. Most preferred as a carbon substrate is glucose.

In addition to an appropriate carbon source, fermentation media must contain suitable minerals, salts, cofactors, buffers and other components, known to those skilled in the art, suitable for the growth of the cultures and promotion of the enzymatic pathway necessary for glycerol production.

Culture Conditions

Typically cells are grown at 30° C. in appropriate media. Preferred growth media are common commercially prepared media such as Luria Bertani (LB) broth, Sabouraud Dextrose (SD) broth, or Yeast medium (YM) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 2':3'-mono-phosphate, may also be incorporated into the reaction media. Similarly, the use of agents known to modulate enzymatic activities (e.g., sulfites, bisulfites, and alkalis) that lead to enhancement of glycerol production may be used in conjunction with or as an alternative to genetic manipulations.

Suitable pH ranges for the fermentation are between pH 5.0 to pH 9.0 where the range of pH 6.0 to pH 8.0 is preferred for the initial condition.

Reactions may be performed under aerobic or anaerobic conditions where anaerobic or microaerobic conditions are preferred.

Identification and Purification of G3PDH and G3P Phosphatase

The levels of expression of the proteins G3PDH and G3P phosphatase are measured by enzyme assays. G3PDH activity assay relies on the spectral properties of the cosubstrate, NADH, in the DHAP conversion to G-3-P. NADH has intrinsic UV/vis absorption and its consumption can be monitored spectro-photometrically at 340 nm. G3P phosphatase activity can be measured by any method of measuring the inorganic phosphate liberated in the reaction. The most commonly used detection method uses the visible spectroscopic determination of a blue-colored phosphomolybdate ammonium complex.

Identification and Recovery of Glycerol

Glycerol may be identified and quantified by high performance liquid chromatography (HPLC) and gas chromatography/mass spectroscopy (GC/MS) analyses on the cell-free extracts. Preferred is a method where the fermentation media are analyzed on an analytical ion exchange column using a mobile phase of 0.1N sulfuric acid in an isocratic fashion.

Methods for the recovery of glycerol from fermentation media are known in the art. For example, glycerol can be obtained from cell media by subjecting the reaction mixture to the following sequence of steps: filtration; water removal; organic solvent extraction, and fractional distillation (U.S. Pat. No. 2,986,495).

Selection of Transformants by Complementation

In the absence of a functional gpsA-encoded G3PDH, *E. coli* cells are unable to synthesize G3P, a condition which leads to a block in membrane biosynthesis. Cells with such a block are auxotrophic, requiring that either glycerol or G3P be present in the culture media for synthesis of membrane phospholipids.

A cloned heterologous wild-type gpsA gene is able to complement the chromosomal gpsA mutation to allow growth in media lacking glycerol or G3P (Wang, et al. (1994), *J. Bact.* 176:7091–7095). Based on this complementation strategy, growth of gpsA-defective cells on glucose would only occur if they possessed a plasmid-encoded gpsA, allowing a selection based on synthesis of G3P from DHAP. Cells which lose the recombinant gpsA plasmid during culture would fail to synthesize G3P and cell growth would subsequently be inhibited. The complementing G3PDH activity can be expressed not only from gpsA, but also from other cloned genes expressing G3PDH activity such as GPD1, GPD2, GPD3, GUT2, glpD, and glpABC. These can be maintained in a gpsA-defective *E. coli* strain such as BB20 (Cronan et al. (1974), *J. Bact.*, 118:598), alleviating the need to use antibiotic selection and its prohibitive cost in large-scale fermentations.

A related strategy can be used for expression and selection in osmoregulatory mutants of *S. cerevisiae* (Larsson et al. (1993), *Mol. Microbiol.*, 10:1101–1111). These osg1 mutants are unable to grow at low water potential and show a decreased capacity for glycerol production and reduced G3PDH activity. The osg1 salt sensitivity defect can be complemented by a cloned and expressed G3PDH gene. Thus, the ability to synthesize glycerol can be used simultaneously as a selection marker for the desired glycerol-producing cells.

EXAMPLES

GENERAL METHODS

Procedures for phosphorylations ligations and transformations are well known in the art. Techniques suitable for use in the following examples may be found in Sambrook et al., *Molecular Cloning: A Laboratory Manual*, Second Edition, Cold Spring Harbor Laboratory Press (1989).

Materials and methods suitable for the maintenance and growth of bacterial cultures are well known in the art. Techniques suitable for use in the following examples may be found in *Manual of Methods for General Bacteriology* (Phillipp Gerhardt. R. G. E. Murray, Ralph N. Costilow, Eugene W. Nester. Willis A. Wood, Noel R. Krieg and G. Briggs Phillips eds), American Society for Microbiology, Washington, DC. (1994) or in *Biotechnology: A Textbook of Industrial Microbioloy* (Thomas D. Brock, Second Edition (1989) Sinauer Associates. Inc., Sunderland. Mass.). All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis. Mo.) unless otherwise specified.

The meaning of abbreviations is as follows: "h" means hour(s), "min" means minute(s), "sec" means second(s), "d" means day(s), "mL" means milliliters, "L" means liters.

Cell Strains

The following *Escherichia coli* strains were used for transformation and expression of G3PDH and G3P phosphatase. Strains were obtained from the *E. coli* Genetic Stock Center or from Life Technologies, Gaithersburg, Md.).

AA200 (garB10 fhuA22 ompF627 fadL701 relA1 pit-10 spoT1 tpi-1 phoM510 mcrB1) (Anderson et al., (1970), *J. Gen. Microbiol.*, 62:329).

BB20 (tonA22 ΔphoA8 fadL701 relA1 glpR2 glpD3 pit-10 gpsA20 spoT1 T2R) (Cronan et al., *J. Bact.*, 118:598).

DH5α (deoR endA1 gyrA96 hsdR17 recA1 relA1 supE44 thi-1 Δ(lacZYA-a)gFV169) phi80lacZΔM15 F−) (Woodcock et al., (1989), *Nucl. Acids Res.* 17:3469).

Identification of Glycerol

The conversion of glucose to glycerol was monitored by HPLC and/or GC. Analyses were performed using standard techniques and materials available to one of skill in the art of chromatography. One suitable method utilized a Waters Maxima 820 HPLC system using UV (210 nm) and RI detection. Samples were injected onto a Shodex SH-1011 column (8 mm×300 mm; Waters. Milford, Mass.) equipped with a Shodex SH-1011P precolumn (6 mm×50 mm), temperature-controlled at 50° C., using 0.01 N $H_2SO_4$ as mobile phase at a flow rate of 0.5 mL/min. When quantitative analysis was desired, samples were injected onto a Shodex SH-1011 column (8 mm×300 mm: Waters, Milford, Mass.) equipped with a Shodex SH-1011P precolumn (6 mm×50 mm), temperature-controlled at 50° C., using 0.01 N $H_2SO_4$ as mobile phase at a flow rate of 0.69 mL/min. When quantitative analysis was desired, samples were prepared with a known amount of trimethylacetic acid as an external standard. Typically, the retention times of glycerol (RI detection) and glucose (RI detection) were 17.03 min and 12.66 min. respectively.

Glycerol was also analyzed by GC/MS. Gas chromatography with mass spectrometry detection for and quantitation of glycerol was done using a DB-WAX column (30 m. 0.32 mm I.D., 0.25 um film thickness, J & W Scientific, Folsom, Calif.), at the following conditions: injector: split, 1:15; sample volume: 1 uL; temperature profile: 150° C. intitial temperature with 30 sec hold, 40° C./min to 180° C., 20° C./min to 240° C. hold for 2.5 min. Detection: El Mass Spectrometry (Hewlett Packard 5971, San Fernando, Calif.), quantitative SIM using ions 61 m/z and 64 m/z as target ions for glycerol and glycerol-d8, and ion 43 m/z as qualifier ion for glycerol. Glycerol-d8 was used as an internal standard.

Assay for glycerol-3-Dhosphatase, GPP

The assay for enzyme activity was performed by incubating the extract with an organic phosphate substrate in a bis-Tris or MES and magnesium buffer, pH 6.5. The substrate used was either 1-α-glycerol phosphate, or d,1-α-glycerol phosphate. The final concentrations of the reagents in the assay are: buffer (20 mM, bis-Tris or 50 mM MES); $MgCl_2$ (10 mM); and substrate (20 mM). If the total protein in the sample was low and no visible precipitation occurs with an acid quench, the sample was conveniently assayed in the cuvette. This method involved incubating an enzyme sample in a cuvette that contained 20 mM substrate (50 μL, 200 mM), 50 mM MES, 10 mM $MgCl_2$, pH 6.5 buffer. The final phosphatase assay volume was 0.5 mL. The enzyme-containing sample was added to the reaction mixture: the contents of the cuvette were mixed and then the cuvette was placed in a circulating water bath at T=37° C. for 5 to 120 min, the length of time depending on whether the phosphatase activity in the enzyme sample ranged from 2 to 0.02 U/mL. The enzymatic reaction was quenched by the addition of the acid molybdate reagent (0.4 mL). After the Fiske SubbaRow reagent (0.1 mL) and distilled water (1.5 mL) were added, the solution was mixed and allowed to develop. After 10 min, to allow full color development, the absorbance of the samples was read at 660 nm using a Cary 219 UV/Vis spectrophotometer. The amount of inorganic phosphate released was compared to a standard curve that was prepared by using a stock inorganic phosphate solution (0.65 mM) and preparing 6 standards with final inorganic phosphate concentrations ranging from 0.026 to 0.130 μmol/mL.

Spectronhotometric Assay for Glycerol 3-Phosohate Dehydrogenase (G3PDH) Activity The following procedure was used as modified below from a method published by Bell et al. (1975), *J. Biol. Chem.*, 250:7153–8. This method involved incubating an enzyme sample in a cuvette that contained 0.2 mM NADH, 2.0 mM Dihydroxyacetone phosphate (DHAP), and enzyme in 0.1 M Tris/HCl, pII 7.5 buffer with 5 mM DTT, in a total volume of 1.0 mL at 30° C. The spectrophotometer was set to monitor absorbance changes at the fixed wavelength of 340 nm. The instrument was blanked on a cuvette containing buffer only. After the enzyme was added to the cuvette, an absorbance reading was taken. The first substrate, NADH (50 uL 4 mM NADH; absorbance should increase approx 1.25 AU), was added to determine the background rate. The rate should be followed for at least 3 min. The second substrate. DHAP (50 uL 40 mM DHAP). was then added and the absorbance change over time was monitored for at least 3 min to determine to determine the gross rate. G3PDH activity was defined by subtracting the background rate from the gross rate.

PLASMID CONSTRUCTION AND STRAIN CONSTRUCTION

Cloning and Expression of Glycerol 3-phosphatase for Increase of Glycerol Production in *E. Coli*

The *Saccharomyces cerevisiae* chromosome V lamda clone 6592 (Gene Bank, accession # U18813×11) was obtained from ATCC. The glycerol 3-phosphate phosphatase (GPP2) gene was cloned by cloning from the lamda clone as target DNA using synthetic primers (SEQ ID NO:16 with SEQ ID NO:17) incorporating an BamHI-RBS-XbaI site at the 5' end and a SmaI site at the 3' end. The product was subcloned into pCR-Script (Stratagene, Madison, Wis.) at the SrfI site to generate the plasmids pAH15 containing GPP2. The plasmid pAH 15 contains the GPP2 gene in the inactive orientation for expression from the lac promoter in pCR-Script SK+. The BamHI-SmaI fragment from pAH15 containing the GPP2 gene was inserted into pBlueScriptII SK+ to generate plasmid pAH 19. The pAH19 contains the GPP2 gene in the correct orientation for expression from the lac promoter. The XbaI-PstI fragment from pAH 19 containing the GPP2 gene was inserted into pPHOX2 to create plasmid pAH21. The pAH21/DH5α is the expression plasmid.

Plasmids for the Over-expression of DAR1 in *E. Coli*

DAR1 was isolated by PCR cloning from genomic *S. cerevisiae* DNA using synthetic primers (SEQ ID NO:18 with SEQ ID NO:19). Successful PCR cloning places an NcoI site at the 5' end of DAR1 where the ATG within NcoI is the DAR1 initiator methionine. At the 3' end of DAR1 a BamHI site is introduced following the translation terminator. The PCR fragments were digested with NcoI +BamHI and cloned into the same sites within the expression plasmid pTrc99A (Pharmacia, Piscataway, N.J.) to give pDAR1A.

In order to create a better ribosome binding site at the 5' end of DAR1, an SpeI-RBS-NcoI linker obtained by annealing synthetic primers (SEQ ID NO:20 with SEQ ID NO:21) was inserted into the NcoI site of pDAR1A to create pAH40. Plasmid pAH40 contains the new RBS and DAR1 gene in the correct orientation for expression from the trc promoter of pTrc99A (Pharmacia, Piscataway, N.J.). The NcoI-BamHI fragment from pDAR1A and an second set of SpeI-RBS-NcoI linker obtained by annealing synthetic primers (SEQ ID NO:22 with SEQ ID NO:23) was inserted into the SpeI-BamHI site of pBC-SK+ (Stratagene, Madison, Wis.) to create plasmid pAH42. The plasmid pAH42 contains a chloramphenicol resistant gene.

Construction of Expression Cassettes for DAR1 and GPP2

Expression cassettes for DAR1 and GPP2 were assembled from the individual DAR1 and GPIP2 subclones described above using standard molecular biology methods. The BamHI-PstI fragment from pAH19 containing the ribosomal binding site (RBS) and GPP2 gene was inserted into pAH40 to create pAH43. The BamHI-PstI fragment from pAH19 containing the RBS and GPP2 gene was inserted into pAH42 to create pAH45.

The ribosome binding site at the 5' end of GPP2 was modified as follows. A BamHI-RBS-SpeI linker, obtained by annealing synthetic primers GATCCAGGAAACAGA (SEQ ID NO:24) with CTAGTCTGTTFTCCTG (SEQ ID NO:25) to the XbaI-PstI fragment from pAH19 containing the GPP2 gene, was inserted into the BamHI-PstI site of pAH40 to create pAH48. Plasmid pAH48 contains the DAR1 genes the modified RBS, and the GPP2 gene in the correct orientation for expression from the trc promoter of pTrc99A (Pharmacia Piscataway, N.J.).

Transformation of *E. Coli*

All the plasmids described here were transformed into *E. coli* DH5α using standard molecular biology techniques. The transformants were verified by its DNA RFLP pattern.

EXAMPLE 1

PRODUCTION OF GLYCEROL FROM *E. COLI* TRANSFORMED WITH G3PDH GENE

Media

Synthetic media was used for anaerobic or aerobic production of glycerol using *E. coli* cells transformed with pDAR1 A. The media contained per liter 6.0 g $Na_2HPO_4$, 3.0 g $KH_2PO_4$, 1.0 g $NH_4Cl$, 0.5 g NaCl, 1 mL 20% $MgSO_4$, $7H_2O$, 8.0 g glucose, 40 mg casamino acids 0.5 ml 1% thiamine hydrochloride, 100 mg ampicillin.

Growth Conditions

Strain AA200 harboring pDAR1A or the pTrc99A vector was grown in aerobic conditions in 50 mL of media shaking at 250 rpm in 250 mL flasks at 37° C. At $A_{600}$ 0.2–0.3 isopropylthio-β-D-galactoside was added to a final concentration of 1 mM and incubation continued for 48 h. For anaerobic growth samples of induced cells were used to fill Falcon #2054 tubes which were capped and gently mixed by rotation at 37° C. for 48 h. Glycerol production was determined by HPLC analysis of the culture supernatants. Strain pDAR1A/AA200 produced 0.38 g/L glycerol after 48 h under anaerobic conditions, and 0.48 g/L under aerobic conditions.

EXAMPLE 2

PRODUCTION OF GLYCEROL FROM *E. COLI* TRANSFORMED WITH G3P PHOSPHATASE GENE (GPP2)

Media

Synthetic phoA media was used in shake flasks to demonstrate the increase of glycerol by GPP2 expression in *E. coli*. The phoA medium contained per liter: Amisoy, 12 g; ammonium sulfate. 0.62 g; MOPS, 10.5 g, Na-citrate, 1.2 g; NaOH (1 M), 10 mL. 1 M $MgSO_4$, 12 mL; 100X trace elements, 12 mL; 50% glucose. 10 mL; 1% thiamine, 10 mL; 100 mg/mL L-proline, 10 mL, 2.5 mM $FeCl_3$, 5 mL; mixed phosphates buffer, 2 mL (5 mL 0.2 M $NaH_2PO_4$+9 mL 0.2 M $K_2HPO_4$), and pH to 7.0. The 100X traces elements for phoA medium/L contained: $ZnSO_4.7 H_2O$, 0.58 g; $MnSO_4.H_2O$, 0.34 g; $CuSO_4.5 H_2O$, 0.49 g; $CoCl_2.6 H_2O$, 0.47 g: $H_3BO_3$, 0.12 g. $NaMoO_4.2 H_2O$, 0.48 g.

Shake Flasks Experiments

The strains pAH21/DH5α (containing GPP2 gene) and pPHOX2/DH5α (control) were grown in 45 mL of media (phoA media. 50 ug/mL carbenicillin, and 1 ug/mL vitamin $B_{12}$) in a 250 mL shake flask at 37° C. The cultures were grown under aerobic condition (250 rpm shaking) for 24 h. Glycerol production was determined by HPLC analysis of the culture supernatant. pAH21/DH5α produced 0.2 g/L glycerol after 24 h.

EXAMPLE 3

PRODUCTION OF GLYCEROL FROM D-GLUCOSE USING RECOMBINANT E. coli CONTAINING BOTH GPP2 AND DAR1

Growth for demonstration of increased glycerol production by *E. coli* DH5α-containing pAH43 proceeds aerobically at 37° C. in shake-flask cultures (erlenmeyer flasks, liquid volume ⅕th of total volume).

Cultures in minimal media/1% glucose shake-flasks are started by inoculation from overnight LB/1% glucose culture with antibiotic selection. Minimal media are: filter-sterilized defined media, final pH 6.8 (HCl), contained per liter: 12.6 g $(NH_4)_2SO_4$, 13.7 g $K_2HPO_4$, 0.2 g yeast extract (Difco), 1 g $NaHCO_3$, 5 mg vitamin $B_{12}$, 5 mL Modified Balch's Trace-Element Solution (the composition of which can be found in *Methods for General and Molecular Bacteriology* (P. Gerhardt et al., eds, p. 158, American Society for Microbiology, Washington, D.C. (1994)). The shake-flasks are incubated at 37° C. with vigorous shaking for overnight, after which they are sampled for GC analysis of the supernatant. The pAH43/DH5α showed glycerol production of 3.8 g/L after 24 h.

EXAMPLE 4

PRODUCTION OF GLYCEROL FROM D-GLUCOSE USING RECOMBINANT *E. COLI* CONTAINING BOTH GPP2 AND DAR1

Example 4 illustrates the production of glucose from the recombinant *E. coli* DH5α/pAH48, containing both the GPP2 and DAR1 genes.

The strain DH5a/pAH48 was constructed as described above in the

GENERAL METHODS

Pre-Culture

DH5α/pAH48 were pre-cultured for seeding into a fermentation run. Components and protocols for the pre-culture are listed below.

| Pre-Culture Media | |
|---|---|
| $KH_2PO_4$ | 30.0 g/L |
| Citric acid | 2.0 g/L |
| $MgSO_4.7H_2O$ | 2.0 g/L |
| 98% $H_2SO_4$ | 2.0 mL/L |
| Ferric ammonium citrate | 0.3 g/L |
| $CaCl_2.2H_2O$ | 0.2 g/L |
| Yeast extract | 5.0 g/L |
| Trace metals | 5.0 mL/L |
| Glucose | 10.0 g/L |
| Carbenicillin | 100.0 mg/L |

The above media components were mixed together and the pH adjusted to 6.8 with $NH_4OH$. The media was then filter sterilized.

Trace metals were used according to the following recipe:

| | |
|---|---|
| Citric acid, monohydrate | 4.0 g/L |
| $MgSO_4.7H_2O$ | 3.0 g/L |
| $MnSO_4.H_2O$ | 0.5 g/L |
| NaCl | 1.0 g/L |
| $FeSO_4.7H_2O$ | 0.1 g/L |
| $CoCl_2.6H_2O$ | 0.1 g/L |
| $CaCl_2$ | 0.1 g/L |
| $ZnSO_4.7H_2O$ | 0.1 g/L |
| $CuSO_4.5H_2O$ | 10 mg/L |
| $AlK(SO_4)_2.12H_2O$ | 10 mg/L |
| $H_3BO_3$ | 10 mg/L |
| $Na_2MoO_4.2H_2O$ | 10 mg/L |
| $NiSO4.6H_2O$ | 10 mg/L |
| $Na_2SeO_3$ | 10 mg/L |
| $Na_2WO_4.2H_2O$ | 10 mg/L |

Cultures were started from seed culture inoculated from 50 µL frozen stock (15% glycerol as cryoprotectant) to 600 mL medium in a 2-L Erlenmeyer flask. Cultures were grown at 30° C. in a shaker at 250 rpm for approximately 12 h and then used to seed the fermenter.

Fermentation Growth Vessel

| Medium | |
|---|---|
| $KH_2PO_4$ | 6.8 g/L |
| Citric acid | 2.0 g/L |
| $MgSO_4.7H_2O$ | 2.0 g/L |
| 98% $H_2SO_4$ | 2.0 mL/L |
| Ferric ammonium citrate | 0.3 g/L |
| $CaCl_2.2H_2O$ | 0.2 g/L |
| Mazu DF204 antifoam | 1.0 mL/L |

The above components were sterilized together in the fermenter vessel. The pH was raised to 6.7 with $NH_4OH$. Yeast extract (5 g/L) and trace metals solution (5 mL/L) were added aseptically from filter sterilized stock solutions. Glucose was added from 60% feed to give final concentration of 10 g/L. Carbenicillin was added at 100 mg/L. Volume after inoculation was 6 L.

Environmental Conditions For Fermentation

The temperature was controlled at 36° C. and the air flow rate was controlled at 6 standard liters per minute. Back pressure was controlled at 0.5 bar. The agitator was set at 350 rpm. Aqueous ammonia was used to control pH at 6.7. The glucose feed (60% glucose monohydrate) rate was controlled to maintain excess glucose.

Results

The results of the fermentation run are given in Table 1.

TABLE 1

| EFT (hr) | OD550 (AU) | [Glucose] (g/L) | [Glycerol] (g/L) | Total Glucose Fed (g) | Total Glycerol Produced (g) |
|---|---|---|---|---|---|
| 0 | 0.8 | 9.3 | | 25 | |
| 6 | 4.7 | 4.0 | 2.0 | 49 | 14 |
| 8 | 5.4 | 0 | 3.6 | 71 | 25 |
| 10 | 6.7 | 0.0 | 4.7 | 116 | 33 |
| 12 | 7.4 | 2.1 | 7.0 | 157 | 49 |
| 14.2 | 10.4 | 0.3 | 10.0 | 230 | 70 |
| 16.2 | 18.1 | 9.7 | 15.5 | 259 | 106 |

TABLE 1-continued

| EFT (hr) | OD550 (AU) | [Glucose] (g/L) | [Glycerol] (g/L) | Total Glucose Fed (g) | Total Glycerol Produced (g) |
|---|---|---|---|---|---|
| 18.2 | 12.4 | 14.5 |  | 305 |  |
| 20.2 | 11.8 | 17.4 | 17.7 | 353 | 119 |
| 22.2 | 11.0 | 12.6 |  | 382 |  |
| 24.2 | 10.8 | 6.5 | 26.6 | 404 | 178 |
| 26.2 | 10.9 | 6.8 |  | 442 |  |
| 28.2 | 10.4 | 10.3 | 31.5 | 463 | 216 |
| 30.2 | 10.2 | 13.1 | 30.4 | 493 | 213 |
| 32.2 | 10.1 | 8.1 | 28.2 | 512 | 196 |
| 34.2 | 10.2 | 3.5 | 33.4 | 530 | 223 |
| 36.2 | 10.1 | 5.8 |  | 548 |  |
| 38.2 | 9.8 | 5.1 | 36.1 | 512 | 233 |

What is claimed is:

1. A method for the production of glycerol from a recombinant microorganism comprising:
   (i) transforming a suitable host cell with an expression cassette comprising
      (a) a gene encoding a NADH-dependent glycerol-3-phosphate dehydrogenase enzyme or a NADPH-dependent glycerol-3-phosphate dehydrogenase enzyme; and
      (b) a gene encoding a polypeptide encoding a glycerol-3-phosphatase (EC 3.1.3.21) enzyme;
   (ii) culturing the transformed host cell of (i) in the presence of at least one carbon source selected from the group consisting of monosaccharides, oligosaccharides, polysaccharides, and single-carbon substrates, whereby glycerol is produced; and
   (iii) recovering the glycerol produced in (ii).

2. A method according to claim 1 wherein the suitable host cell is selected from the group consisting of bacteria and fungi.

3. A method according to claim 2 wherein the suitable host cell is selected from the group consisting of Citrobacter, Enterobacter, Clostridium, Klebsiella, Lactobacillus, Aspergillus, Saccharomyces, Schizosaccharomyces, Zygosaccharomyces, Pichia, Kluyveromyces, Candida, Mucor, Torulopsis, Methylobacter, Escherichia, Salmonella, Bacillus, Streptomyces, and Pseudomonas.

4. A method according to claim 3 wherein the suitable host cell is *E. coli* or Saccharomyces.

5. A method according to claim 1 wherein the carbon source is glucose.

6. A method according to claim 1 wherein the gene encoding a NADH-dependent glycerol-3-phosphate dehydrogenase enzyme or NADPH-dependent glycerol-3-phosphate dehydrogenase enzyme encodes the amino acid sequence given in SEQ ID NO:7, SEQ ID NO:8, or SEQ ID NO:10 and wherein the amino acid sequence encompasses amino acid substitutions, deletions or insertions that do not alter the functional properties of the enzyme.

\* \* \* \* \*

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
        (A) LENGTH: 1380 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

```
CTTTAATTTT CTTTTATCTT ACTCTCCTAC ATAAGACATC AAGAAACAAT TGTATATTGT      60
ACACCCCCCC CCTCCACAAA CACAAATATT GATAATATAA AGATGTCTGC TGCTGCTGAT     120
AGATTAAACT TAACTTCCGG CCACTTGAAT GCTGGTAGAA AGAGAAGTTC CTCTTCTGTT     180
TCTTTGAAGG CTGCCGAAAA GCCTTTCAAG GTTACTGTGA TTGGATCTGG TAACTGGGGT     240
ACTACTATTG CCAAGGTGGT TGCCGAAAAT TGTAAGGGAT ACCCAGAAGT TTTCGCTCCA     300
ATAGTACAAA TGTGGGTGTT CGAAGAAGAG ATCAATGGTG AAAAATTGAC TGAAATCATA     360
AATACTAGAC ATCAAAACGT GAAATACTTG CCTGGCATCA CTCTACCCGA CAATTTGGTT     420
GCTAATCCAG ACTTGATTGA TTCAGTCAAG GATGTCGACA TCATCGTTTT CAACATTCCA     480
CATCAATTTT TGCCCCGTAT CTGTAGCCAA TTGAAAGGTC ATGTTGATTC ACACGTCAGA     540
GCTATCTCCT GTCTAAAGGG TTTTGAAGTT GGTGCTAAAG GTGTCCAATT GCTATCCTCT     600
TACATCACTG AGGAACTAGG TATTCAATGT GGTGCTCTAT CTGGTGCTAA CATTGCCACC     660
GAAGTCGCTC AAGAACACTG GTCTGAAACA ACAGTTGCTT ACCACATTCC AAAGGATTTC     720
AGAGGCGAGG GCAAGGACGT CGACCATAAG GTTCTAAAGG CCTTGTTCCA CAGACCTTAC     780
TTCCACGTTA GTGTCATCGA AGATGTTGCT GGTATCTCCA TCTGTGGTGC TTTGAAGAAC     840
GTTGTTGCCT TAGGTTGTGG TTTCGTCGAA GGTCTAGGCT GGGGTAACAA CGCTTCTGCT     900
GCCATCCAAA GAGTCGGTTT GGGTGAGATC ATCAGATTCG GTCAAATGTT TTTCCCAGAA     960
TCTAGAGAAG AAACATACTA CCAAGAGTCT GCTGGTGTTG CTGATTTGAT CACCACCTGC    1020
GCTGGTGGTA GAAACGTCAA GGTTGCTAGG CTAATGGCTA CTTCTGGTAA GGACGCCTGG    1080
GAATGTGAAA AGGAGTTGTT GAATGGCCAA TCCGCTCAAG GTTTAATTAC CTGCAAAGAA    1140
GTTCACGAAT GGTTGGAAAC ATGTGGCTCT GTCGAAGACT TCCCATTATT TGAAGCCGTA    1200
TACCAAATCG TTTACAACAA CTACCCAATG AAGAACCTGC CGGACATGAT TGAAGAATTA    1260
GATCTACATG AAGATTAGAT TTATTGGAGA AAGATAACAT ATCATACTTC CCCCACTTTT    1320
```

-continued

```
TTCGAGGCTC TTCTATATCA TATTCATAAA TTAGCATTAT GTCATTTCTC ATAACTACTT      1380
```

(2) INFORMATION FOR SEQ ID NO: 2:

(i) SEQUENCE CHARACTERISTICS:
        (A) LENGTH: 2946 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

```
GAATTCGAGC CTGAAGTGCT GATTACCTTC AGGTAGACTT CATCTTGACC CATCAACCCC        60
AGCGTCAATC CTGCAAATAC ACCACCCAGC AGCACTAGGA TGATAGAGAT AATATAGTAC       120
GTGGTAACGC TTGCCTCATC ACCTACGCTA TGGCCGGAAT CGGCAACATC CCTAGAATTG       180
AGTACGTGTG ATCCGGATAA CAACGGCAGT GAATATATCT TCGGTATCGT AAAGATGTGA       240
TATAAGATGA TGTATACCCA ATGAGGAGCG CCTGATCGTG ACCTAGACCT TAGTGGCAAA       300
AACGACATAT CTATTATAGT GGGGAGAGTT TCGTGCAAAT AACAGACGCA GCAGCAAGTA       360
ACTGTGACGA TATCAACTCT TTTTTTATTA TGTAATAAGC AAACAAGCAC GAATGGGGAA       420
AGCCTATGTG CAATCACCAA GGTCGTCCCT TTTTTCCCAT TTGCTAATTT AGAATTTAAA       480
GAAACCAAAA GAATGAAGAA AGAAAACAAA TACTAGCCCT AACCCTGACT TCGTTTCTAT       540
GATAATACCC TGCTTTAATG AACGGTATGC CCTAGGGTAT ATCTCACTCT GTACGTTACA       600
AACTCCGGTT ATTTTATCGG AACATCCGAG CACCCGCGCC TTCCTCAACC CAGGCACCGC       660
CCCAGGTAAC CGTGCGCGAT GAGCTAATCC TGAGCCATCA CCCACCCCAC CCGTTGATGA       720
CAGCAATTCG GGAGGGCGAA AATAAAACTG GAGCAAGGAA TTACCATCAC CGTCACCATC       780
ACCATCATAT CGCCTTAGCC TCTAGCCATA GCCATCATGC AAGCGTGTAT CTTCTAAGAT       840
TCAGTCATCA TCATTACCGA GTTTGTTTTC CTTCACATGA TGAAGAAGGT TTGAGTATGC       900
TCGAAACAAT AAGACGACGA TGGCTCTGCC ATTGGTTATA TTACGCTTTT GCGGCGAGGT       960
GCCGATGGGT TGCTGAGGGG AAGAGTGTTT AGCTTACGGA CCTATTGCCA TTGTTATTCC      1020
GATTAATCTA TTGTTCAGCA GCTCTTCTCT ACCCTGTCAT TCTAGTATTT TTTTTTTTTT      1080
TTTTTGGTTT TACTTTTTTT TCTTCTTGCC TTTTTTTCTT GTTACTTTTT TTCTAGTTTT      1140
TTTTCCTTCC ACTAAGCTTT TTCCTTGATT TATCCTTGGG TTCTTCTTTC TACTCCTTTA      1200
GATTTTTTTT TTATATATTA ATTTTTAAGT TTATGTATTT TGGTAGATTC AATTCTCTTT      1260
CCCCTTTCCTT TTCCTTCGCT CCCCTTCCTT ATCAATGCTT GCTGTCAGAA GATTAACAAG      1320
ATACACATTC CTTAAGCGAA CGCATCCGGT GTTATATACT CGTCGTGCAT ATAAAATTTT      1380
GCCTTCAAGA TCTACTTTCC TAAGAAGATC ATTATTACAA ACACAACTGC ACTCAAAGAT      1440
GACTGCTCAT ACTAATATCA AACAGCACAA ACACTGTCAT GAGGACCATC CTATCAGAAG      1500
ATCGGACTCT GCCGTGTCAA TTGTACATTT GAAACGTGCG CCCTTCAAGG TTACAGTGAT      1560
TGGTTCTGGT AACTGGGGGA CCACCATCGC CAAAGTCATT GCGGAAAACA CAGAATTGCA      1620
TTCCCATATC TTCGAGCCAG AGGTGAGAAT GTGGGTTTTT GATGAAAAGA TCGGCGACGA      1680
AAATCTGACG GATATCATAA ATACAAGACA CCAGAACGTT AAATATCTAC CCAATATTGA      1740
CCTGCCCCAT AATCTAGTGG CCGATCCTGA TCTTTTACAC TCCATCAAGG GTGCTGACAT      1800
CCTTGTTTTC AACATCCCTC ATCAATTTTT ACCAAACATA GTCAAACAAT TGCAAGGCCA      1860
CGTGGCCCCT CATGTAAGGG CCATCTCGTG TCTAAAAGGG TTCGAGTTGG GCTCCAAGGG      1920
```

```
TGTGCAATTG CTATCCTCCT ATGTTACTGA TGAGTTAGGA ATCCAATGTG GCGCACTATC    1980

TGGTGCAAAC TTGGCACCGG AAGTGGCCAA GGAGCATTGG TCCGAAACCA CCGTGGCTTA    2040

CCAACTACCA AAGGATTATC AAGGTGATGG CAAGGATGTA GATCATAAGA TTTTGAAATT    2100

GCTGTTCCAC AGACCTTACT TCCACGTCAA TGTCATCGAT GATGTTGCTG GTATATCCAT    2160

TGCCGGTGCC TTGAAGAACG TCGTGGCACT TGCATGTGGT TTCGTAGAAG GTATGGGATG    2220

GGGTAACAAT GCCTCCGCAG CCATTCAAAG GCTGGGTTTA GGTGAAATTA TCAAGTTCGG    2280

TAGAATGTTT TTCCCAGAAT CCAAAGTCGA GACCTACTAT CAAGAATCCG CTGGTGTTGC    2340

AGATCTGATC ACCACCTGCT CAGGCGGTAG AAACGTCAAG GTTGCCACAT ACATGGCCAA    2400

GACCGGTAAG TCAGCCTTGG AAGCAGAAAA GGAATTGCTT AACGGTCAAT CCGCCCAAGG    2460

GATAATCACA TGCAGAGAAG TTCACGAGTG GCTACAAACA TGTGAGTTGA CCCAAGAATT    2520

CCCAATTATT CGAGGCAGTC TACCAGATAG TCTACAACAA CGTCCGCATG GAAGACCTAC    2580

CGGAGATGAT TGAAGAGCTA GACATCGATG ACGAATAGAC ACTCTCCCCC CCCCTCCCCC    2640

TCTGATCTTT CCTGTTGCCT CTTTTTCCCC CAACCAATTT ATCATTATAC ACAAGTTCTA    2700

CAACTACTAC TAGTAACATT ACTACAGTTA TTATAATTTT CTATTCTCTT TTTCTTTAAG    2760

AATCTATCAT TAACGTTAAT TTCTATATAT ACATAACTAC CATTATACAC GCTATTATCG    2820

TTTACATATC ACATCACCGT TAATGAAAGA TACGACACCC TGTACACTAA CACAATTAAA    2880

TAATCGCCAT AACCTTTTCT GTTATCTATA GCCCTTAAAG CTGTTTCTTC GAGCTTTTCA    2940

CTGCAG                                                               2946

(2) INFORMATION FOR SEQ ID NO: 3:

(i) SEQUENCE CHARACTERISTICS:
        (A) LENGTH: 3178 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

CTGCAGAACT TCGTCTGCTC TGTGCCCATC CTCGCGGTTA GAAAGAAGCT GAATTGTTTC      60

ATGCGCAAGG GCATCAGCGA GTGACCAATA ATCACTGCAC TAATTCCTTT TTAGCAACAC     120

ATACTTATAT ACAGCACCAG ACCTTATGTC TTTTCTCTGC TCCGATACGT TATCCCACCC     180

AACTTTTATT TCAGTTTTGG CAGGGGAAAT TTCACAACCC CGCACGCTAA AAATCGTATT     240

TAAACTTAAA AGAGAACAGC CACAAATAGG GAACTTTGGT CTAAACGAAG GACTCTCCCT     300

CCCTTATCTT GACCGTGCTA TTGCCATCAC TGCTACAAGA CTAAATACGT ACTAATATAT     360

GTTTTCGGTA ACGAGAAGAA GAGCTGCCGG TGCAGCTGCT GCCATGGCCA CAGCCACGGG     420

GACGCTGTAC TGGATGACTA GCCAAGGTGA TAGGCCGTTA GTGCACAATG ACCCGAGCTA     480

CATGGTGCAA TTCCCCACCG CCGCTCCACC GGCAGGTCTC TAGACGAGAC CTGCTGGACC     540

GTCTGGACAA GACGCATCAA TTCGACGTGT TGATCATCGG TGGCGGGGCC ACGGGGACAG     600

GATGTGCCCT AGATGCTGCG ACCAGGGGAC TCAATGTGGC CCTTGTTGAA AAGGGGGATT     660

TTGCCTCGGG AACGTCGTCC AAATCTACCA AGATGATTCA CGGTGGGGTG CGGTACTTAG     720

AGAAGGCCTT CTGGGAGTTC TCCAAGGCAC AACTGGATCT GGTCATCGAG GCACTCAACG     780

AGCGTAAACA TCTTATCAAC ACTGCCCCTC ACCTGTGCAC GGTGCTACCA ATTCTGATCC     840

CCATCTACAG CACCTGGCAG GTCCCGTACA TCTATATGGG CTGTAAATTC TACGATTTCT     900
```

-continued

```
TTGGCGGTTC CCAAAACTTG AAAAAATCAT ACCTACTGTC CAAATCCGCC ACCGTGGAGA    960

AGGCTCCCAT GCTTACCACA GACAATTTAA AGGCCTCGCT TGTGTACCAT GATGGGTCCT   1020

TTAACGACTC GCGTTTGAAC GCCACTTTAG CCATCACGGG TGTGGAGAAC GGCGCTACCG   1080

TCTTGATCTA TGTCGAGGTA CAAAAATTGA TCAAAGACCC AACTTCTGGT AAGGTTATCG   1140

GTGCCGAGGC CCGGGACGTT GAGACTAATG AGCTTGTCAG AATCAACGCT AAATGTGTGG   1200

TCAATGCCAC GGGCCCATAC AGTGACGCCA TTTTGCAAAT GGACCGCAAC CCATCCGGTC   1260

TGCCGGACTC CCCGCTAAAC GACAACTCCA AGATCAAGTC GACTTTCAAT CAAATCTCCG   1320

TCATGGACCC GAAAATGGTC ATCCCATCTA TTGGCGTTCA CATCGTATTG CCCTCTTTTT   1380

ACTCCCCGAA GGATATGGGT TTGTTGGACG TCAGAACCTC TGATGGCAGA GTGATGTTCT   1440

TTTTACCTTG GCAGGGCAAA GTCCTTGCCG GCACCACAGA CATCCCACTA AGCAAGTCC    1500

CAGAAAACCC TATGCCTACA GAGGCTGATA TTCAAGATAT CTTGAAAGAA CTACAGCACT   1560

ATATCGAATT CCCCGTGAAA AGAGAAGACG TGCTAAGTGC ATGGGCTGGT GTCAGACCTT   1620

TGGTCAGAGA TCCACGTACA ATCCCCGCAG ACGGGAAGAA GGGCTCTGCC ACTCAGGGCG   1680

TGGTAAGATC CCACTTCTTG TTCACTTCGG ATAATGGCCT AATTACTATT GCAGGTGGTA   1740

AATGGACTAC TTCAGACAA ATGGCTGAGG AAACAGTCGA CAAAGTTGTC GAAGTTGGCG    1800

GATTCCACAA CCTGAAACCT TGTCACACAA GAGATATTAA GCTTGCTGGT GCAGAAGAAT   1860

GGACGCAAAA CTATGTGGCT TTATTGGCTC AAAACTACCA TTTATCATCA AAAATGTCCA   1920

ACTACTTGGT TCAAAACTAC GGAACCCGTT CCTCTATCAT TTGCGAATTT TCAAAGAAT    1980

CCATGGAAAA TAAACTGCCT TTGTCCTTAG CCGACAAGGA AAATAACGTA ATCTACTCTA   2040

GCGAGGAGAA CAACTTGGTC AATTTTGATA CTTTCAGATA TCCATTCACA ATCGGTGAGT   2100

TAAAGTATTC CATGCAGTAC GAATATTGTA GAACTCCCTT GGACTTCCTT TTAAGAAGAA   2160

CAAGATTCGC CTTCTTGGAC GCCAAGGAAG CTTTGAATGC CGTGCATGCC ACCGTCAAAG   2220

TTATGGGTGA TGAGTTCAAT TGGTCGGAGA AAAAGAGGCA GTGGGAACTT GAAAAAACTG   2280

TGAACTTCAT CCAAGGACGT TTCGGTGTCT AAATCGATCA TGATAGTTAA GGGTGACAAA   2340

GATAACATTC ACAAGAGTAA TAATAATGGT AATGATGATA ATAATAATAA TGATAGTAAT   2400

AACAATAATA ATAATGGTGG TAATGGCAAT GAAATCGCTA TTATTACCTA TTTTCCTTAA   2460

TGGAAGAGTT AAAGTAAACT AAAAAAACTA CAAAATATA TGAAGAAAAA AAAAAAAGA     2520

GGTAATAGAC TCTACTACTA CAATTGATCT TCAAATTATG ACCTTCCTAG TGTTTATATT   2580

CTATTTCCAA TACATAATAT AATCTATATA ATCATTGCTG GTAGACTTCC GTTTTAATAT   2640

CGTTTTAATT ATCCCCTTTA TCTCTAGTCT AGTTTTATCA TAAAATATAG AAACACTAAA   2700

TAATATTCTT CAAACGGTCC TGGTGCATAC GCAATACATA TTTATGGTGC AAAAAAAAA    2760

ATGGAAAATT TTGCTAGTCA TAAACCCTTT CATAAAACAA TACGTAGACA TCGCTACTTG   2820

AAATTTTCAA GTTTTTATCA GATCCATGTT TCCTATCTGC CTTGACAACC TCATCGTCGA   2880

AATAGTACCA TTTAGAACGC CCAATATTCA CATTGTGTTC AAGGTCTTTA TTCACCAGTG   2940

ACGTGTAATG GCCATGATTA ATGTGCCTGT ATGGTTAACC ACTCCAAATA GCTTATATTT   3000

CATAGTGTCA TTGTTTTTCA ATATAATGTT TAGTATCAAT GGATATGTTA CGACGGTGTT   3060

ATTTTTCTTG GTCAAATCGT AATAAAATCT CGATAAATGG ATGACTAAGA TTTTTGGTAA   3120

AGTTACAAAA TTTATCGTTT TCACTGTTGT CAATTTTTTG TTCTTGTAAT CACTCGAGAG   3178
```

(2) INFORMATION FOR SEQ ID NO: 4:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

```
ATGAAACGTT TCAATGTTTT AAAATATATC AGAACAACAA AAGCAAATAT ACAAACCATC      60

GCAATGCCTT TGACCACAAA ACCTTTATCT TTGAAAATCA ACGCCGCTCT ATTCGATGTT     120

GACGGTACCA TCATCATCTC TCAACCAGCC ATTGCTGCTT TCTGGAGAGA TTTCGGTAAA     180

GACAAGCCTT ACTTCGATGC CGAACACGTT ATTCACATCT CTCACGGTTG GAGAACTTAC     240

GATGCCATTG CCAAGTTCGC TCCAGACTTT GCTGATGAAG AATACGTTAA CAAGCTAGAA     300

GGTGAAATCC CAGAAAAGTA CGGTGAACAC TCCATCGAAG TTCCAGGTGC TGTCAAGTTG     360

TGTAATGCTT TGAACGCCTT GCCAAAGGAA AAATGGGCTG TCGCCACCTC TGGTACCCGT     420

GACATGGCCA AGAAATGGTT CGACATTTTG AAGATCAAGA GACCAGAATA CTTCATCACC     480

GCCAATGATG TCAAGCAAGG TAAGCCTCAC CCAGAACCAT ACTTAAAGGG TAGAAACGGT     540

TTGGGTTTCC CAATTAATGA ACAAGACCCA TCCAAATCTA AGGTTGTTGT CTTTGAAGAC     600

GCACCAGCTG GTATTGCTGC TGGTAAGGCT GCTGGCTGTA AAATCGTTGG TATTGCTACC     660

ACTTTCGATT TGGACTTCTT GAAGGAAAAG GGTTGTGACA TCATTGTCAA GAACCACGAA     720

TCTATCAGAG TCGGTGAATA CAACGCTGAA ACCGATGAAG TCGAATTGAT CTTTGATGAC     780

TACTTATACG CTAAGGATGA CTTGTTGAAA TGGTAA                               816
```

(2) INFORMATION FOR SEQ ID NO: 5:

(i) SEQUENCE CHARACTERISTICS:
        (A) LENGTH: 753 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
ATGGGATTGA CTACTAAACC TCTATCTTTG AAAGTTAACG CCGCTTTGTT CGACGTCGAC      60

GGTACCATTA TCATCTCTCA ACCAGCCATT GCTGCATTCT GGAGGGATTT CGGTAAGGAC     120

AAACCTTATT TCGATGCTGA ACACGTTATC CAAGTCTCGC ATGGTTGGAG AACGTTTGAT     180

GCCATTGCTA AGTTCGCTCC AGACTTTGCC AATGAAGAGT ATGTTAACAA ATTAGAAGCT     240

GAAATTCCGG TCAAGTACGG TGAAAAATCC ATTGAAGTCC CAGGTGCAGT TAAGCTGTGC     300

AACGCTTTGA ACGCTCTACC AAAAGAGAAA TGGGCTGTGG CAACTTCCGG TACCCGTGAT     360

ATGGCACAAA AATGGTTCGA GCATCTGGGA ATCAGGAGAC CAAAGTACTT CATTACCGCT     420

AATGATGTCA AACAGGGTAA GCCTCATCCA GAACCATATC TGAAGGGCAG GAATGGCTTA     480

GGATATCCGA TCAATGAGCA AGACCCTTCC AAATCTAAGG TAGTAGTATT TGAAGACGCT     540

CCAGCAGGTA TTGCCGCCGG AAAAGCCGCC GGTTGTAAGA TCATTGGTAT TGCCACTACT     600

TTCGACTTGG ACTTCCTAAA GGAAAAAGGC TGTGACATCA TTGTCAAAAA CCACGAATCC     660

ATCAGAGTTG GCGGCTACAA TGCCGAAACA GACGAAGTTG AATTCATTTT TGACGACTAC     720

TTATATGCTA AGGACGATCT GTTGAAATGG TAA                                  753
```

(2) INFORMATION FOR SEQ ID NO: 6:

(i) SEQUENCE CHARACTERISTICS:
        (A) LENGTH: 2520 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

```
TGTATTGGCC ACGATAACCA CCCTTTGTAT ACTGTTTTTG TTTTTCACAT GGTAAATAAC      60

GACTTTTATT AAACAACGTA TGTAAAAACA TAACAAGAAT CTACCCATAC AGGCCATTTC     120

GTAATTCTTC TCTTCTAATT GGAGTAAAAC CATCAATTAA AGGGTGTGGA GTAGCATAGT     180

GAGGGGCTGA CTGCATTGAC AAAAAAATTG AAAAAAAAAA AGGAAAAGGA AAGGAAAAAA     240

AGACAGCCAA GACTTTTAGA ACGGATAAGG TGTAATAAAA TGTGGGGGGA TGCCTGTTCT     300

CGAACCATAT AAAATATACC ATGTGGTTTG AGTTGTGGCC GGAACTATAC AAATAGTTAT     360

ATGTTTCCCT CTCTCTTCCG ACTTGTAGTA TTCTCCAAAC GTTACATATT CCGATCAAGC     420

CAGCGCCTTT ACACTAGTTT AAAACAAGAA CAGAGCCGTA TGTCCAAAAT AATGGAAGAT     480

TTACGAAGTG ACTACGTCCC GCTTATCGCC AGTATTGATG TAGGAACGAC CTCATCCAGA     540

TGCATTCTGT TCAACAGATG GGGCCAGGAC GTTTCAAAAC ACCAAATTGA ATATTCAACT     600

TCAGCATCGA AGGGCAAGAT TGGGGTGTCT GGCCTAAGGA GACCCTCTAC AGCCCCAGCT     660

CGTGAAACAC CAAACGCCGG TGACATCAAA ACCAGCGGAA AGCCCATCTT TTCTGCAGAA     720

GGCTATGCCA TTCAAGAAAC CAAATTCCTA AAAATCGAGG AATTGGACTT GGACTTCCAT     780

AACGAACCCA CGTTGAAGTT CCCCAAACCG GGTTGGGTTG AGTGCCATCC GCAGAAATTA     840

CTGGTGAACG TCGTCCAATG CCTTGCCTCA AGTTTGCTCT CTCTGCAGAC TATCAACAGC     900

GAACGTGTAG CAAACGGTCT CCCACCTTAC AAGGTAATAT GCATGGGTAT AGCAAACATG     960

AGAGAAACCA CAATTCTGTG GTCCCGCCGC ACAGGAAAAC CAATTGTTAA CTACGGTATT    1020

GTTTGGAACG ACACCAGAAC GATCAAAATC GTTAGAGACA AATGGCAAAA CACTAGCGTC    1080

GATAGGCAAC TGCAGCTTAG ACAGAAGACT GGATTGCCAT TGCTCTCCAC GTATTTCTCC    1140

TGTTCCAAGC TGCGCTGGTT CCTCGACAAT GAGCCTCTGT GTACCAAGGC GTATGAGGAG    1200

AACGACCTGA TGTTCGGCAC TGTGGACACA TGGCTGATTT ACCAATTAAC TAAACAAAAG    1260

GCGTTCGTTT CTGACGTAAC CAACGCTTCC AGAACTGGAT TTATGAACCT CTCCACTTTA    1320

AAGTACGACA ACGAGTTGCT GGAATTTTGG GGTATTGACA AGAACCTGAT TCACATGCCC    1380

GAAATTGTGT CCTCATCTCA ATACTACGGT GACTTTGGCA TTCCTGATTG GATAATGGAA    1440

AAGCTACACG ATTCGCCAAA AACAGTACTG CGAGATCTAG TCAAGAGAAA CCTGCCCATA    1500

CAGGGCTGTC TGGGCGACCA AAGCGCATCC ATGGTGGGGC AACTCGCTTA CAAACCCGGT    1560

GCTGCAAAAT GTACTTATGG TACCGGTTGC TTTTTACTGT ACAATACGGG GACCAAAAAA    1620

TTGATCTCCC AACATGGCGC ACTGACGACT CTAGCATTTT GGTTCCCACA TTTGCAAGAG    1680

TACGGTGGCC AAAAACCAGA ATTGAGCAAG CCACATTTTG CATTAGAGGG TTCCGTCGCT    1740

GTGGCTGGTG CTGTGGTCCA ATGGCTACGT GATAATTTAC GATTGATCGA TAAATCAGAG    1800

GATGTCGGAC CGATTGCATC TACGGTTCCT GATTCTGGTG GCGTAGTTTT CGTCCCCGCA    1860

TTTAGTGGCC TATTCGCTCC CTATTGGGAC CCAGATGCCA GAGCCACCAT AATGGGGATG    1920

TCTCAATTCA CTACTGCCTC CCACATCGCC AGAGCTGCCG TGGAAGGTGT TTGCTTTCAA    1980

GCCAGGGCTA TCTTGAAGGC AATGAGTTCT GACGCGTTTG GTGAAGGTTC CAAAGACAGG    2040
```

-continued

```
GACTTTTTAG AGGAAATTTC CGACGTCACA TATGAAAAGT CGCCCCTGTC GGTTCTGGCA      2100

GTGGATGGCG GGATGTCGAG GTCTAATGAA GTCATGCAAA TTCAAGCCGA TATCCTAGGT      2160

CCCTGTGTCA AGTCAGAAG GTCTCCGACA GCGGAATGTA CCGCATTGGG GGCAGCCATT       2220

GCAGCCAATA TGGCTTTCAA GGATGTGAAC GAGCGCCCAT TATGGAAGGA CCTACACGAT      2280

GTTAAGAAAT GGGTCTTTTA CAATGGAATG GAGAAAAACG AACAAATATC ACCAGAGGCT      2340

CATCCAAACC TTAAGATATT CAGAAGTGAA TCCGACGATG CTGAAAGGAG AAAGCATTGG      2400

AAGTATTGGG AAGTTGCCGT GGAAAGATCC AAAGGTTGGC TGAAGGACAT AGAAGGTGAA      2460

CACGAACAGG TTCTAGAAAA CTTCCAATAA CAACATAAAT AATTTCTATT AACAATGTAA      2520
```

(2) INFORMATION FOR SEQ ID NO: 7:

(i) SEQUENCE CHARACTERISTICS:
        (A) LENGTH: 391 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 7:

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
            35                  40                  45

Ile Ala Lys Val Val Ala Glu Asn Cys Lys Gly Tyr Pro Glu Val Phe
50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
                100                 105                 110

Asp Ser Val Lys Asp Val Asp Ile Ile Val Phe Asn Ile Pro His Gln
                115                 120                 125

Phe Leu Pro Arg Ile Cys Ser Gln Leu Lys Gly His Val Asp Ser His
130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
                180                 185                 190

Trp Ser Glu Thr Thr Val Ala Tyr His Ile Pro Lys Asp Phe Arg Gly
                195                 200                 205

Glu Gly Lys Asp Val Asp His Lys Val Leu Lys Ala Leu Phe His Arg
                210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
```

-continued

```
                    260                 265                 270
Leu Gly Glu Ile Ile Arg Phe Gly Gln Met Phe Phe Pro Glu Ser Arg
                275                 280                 285
Glu Glu Thr Tyr Tyr Gln Glu Ser Ala Gly Val Ala Asp Leu Ile Thr
290                 295                 300
Thr Cys Ala Gly Gly Arg Asn Val Lys Val Ala Arg Leu Met Ala Thr
305                 310                 315                 320
Ser Gly Lys Asp Ala Trp Glu Cys Glu Lys Glu Leu Leu Asn Gly Gln
                325                 330                 335
Ser Ala Gln Gly Leu Ile Thr Cys Lys Glu Val His Glu Trp Leu Glu
                340                 345                 350
Thr Cys Gly Ser Val Glu Asp Phe Pro Leu Phe Glu Ala Val Tyr Gln
                355                 360                 365
Ile Val Tyr Asn Asn Tyr Pro Met Lys Asn Leu Pro Asp Met Ile Glu
370                 375                 380
Glu Leu Asp Leu His Glu Asp
385                 390
```

(2) INFORMATION FOR SEQ ID NO: 8:

(i) SEQUENCE CHARACTERISTICS:
        (A) LENGTH: 384 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 8:

```
Met Thr Ala His Thr Asn Ile Lys Gln His Lys His Cys His Glu Asp
1               5                   10                  15
His Pro Ile Arg Arg Ser Asp Ser Ala Val Ser Ile Val His Leu Lys
                20                  25                  30
Arg Ala Pro Phe Lys Val Thr Val Ile Gly Ser Gly Asn Trp Gly Thr
                35                  40                  45
Thr Ile Ala Lys Val Ile Ala Glu Asn Thr Glu Leu His Ser His Ile
                50                  55                  60
Phe Glu Pro Glu Val Arg Met Trp Val Phe Asp Glu Lys Ile Gly Asp
65                  70                  75                  80
Glu Asn Leu Thr Asp Ile Ile Asn Thr Arg His Gln Asn Val Lys Tyr
                85                  90                  95
Leu Pro Asn Ile Asp Leu Pro His Asn Leu Val Ala Asp Pro Asp Leu
                100                 105                 110
Leu His Ser Ile Lys Gly Ala Asp Ile Leu Val Phe Asn Ile Pro His
                115                 120                 125
Gln Phe Leu Pro Asn Ile Val Lys Gln Leu Gln Gly His Val Ala Pro
                130                 135                 140
His Val Arg Ala Ile Ser Cys Leu Lys Gly Phe Glu Leu Gly Ser Lys
145                 150                 155                 160
Gly Val Gln Leu Leu Ser Ser Tyr Val Thr Asp Glu Leu Gly Ile Gln
                165                 170                 175
Cys Gly Ala Leu Ser Gly Ala Asn Leu Ala Pro Glu Val Ala Lys Glu
                180                 185                 190
His Trp Ser Glu Thr Thr Val Ala Tyr Gln Leu Pro Lys Asp Tyr Gln
                195                 200                 205
Gly Asp Gly Lys Asp Val Asp His Lys Ile Leu Lys Leu Leu Phe His
```

-continued

```
            210                 215                 220
Arg Pro Tyr Phe His Val Asn Val Ile Asp Asp Val Ala Gly Ile Ser
225                 230                 235                 240

Ile Ala Gly Ala Leu Lys Asn Val Val Ala Leu Ala Cys Gly Phe Val
                245                 250                 255

Glu Gly Met Gly Trp Gly Asn Asn Ala Ser Ala Ile Gln Arg Leu
            260                 265                 270

Gly Leu Gly Glu Ile Ile Lys Phe Gly Arg Met Phe Phe Pro Glu Ser
                275                 280                 285

Lys Val Glu Thr Tyr Tyr Gln Glu Ser Ala Gly Val Ala Asp Leu Ile
                290                 295                 300

Thr Thr Cys Ser Gly Gly Arg Asn Val Lys Val Ala Thr Tyr Met Ala
305                 310                 315                 320

Lys Thr Gly Lys Ser Ala Leu Glu Ala Glu Lys Glu Leu Leu Asn Gly
                325                 330                 335

Gln Ser Ala Gln Gly Ile Ile Thr Cys Arg Glu Val His Glu Trp Leu
                340                 345                 350

Gln Thr Cys Glu Leu Thr Gln Glu Phe Pro Ile Ile Arg Gly Ser Leu
                355                 360                 365

Pro Asp Ser Leu Gln Gln Arg Pro His Gly Arg Pro Thr Gly Asp Asp
370                 375                 380
```

(2) INFORMATION FOR SEQ ID NO: 9:

(i) SEQUENCE CHARACTERISTICS:
        (A) LENGTH: 614 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 9:

```
Met Thr Arg Ala Thr Trp Cys Asn Ser Pro Pro Leu His Arg Gln
1               5                   10                  15

Val Ser Arg Arg Asp Leu Leu Asp Arg Leu Asp Lys Thr His Gln Phe
                20                  25                  30

Asp Val Leu Ile Ile Gly Gly Gly Ala Thr Gly Thr Gly Cys Ala Leu
                35                  40                  45

Asp Ala Ala Thr Arg Gly Leu Asn Val Ala Leu Val Glu Lys Gly Asp
50                  55                  60

Phe Ala Ser Gly Thr Ser Ser Lys Ser Thr Lys Met Ile His Gly Gly
65                  70                  75                  80

Val Arg Tyr Leu Glu Lys Ala Phe Trp Glu Phe Ser Lys Ala Gln Leu
                85                  90                  95

Asp Leu Val Ile Glu Ala Leu Asn Glu Arg Lys His Leu Ile Asn Thr
                100                 105                 110

Ala Pro His Leu Cys Thr Val Leu Pro Ile Leu Ile Pro Ile Tyr Ser
                115                 120                 125

Thr Trp Gln Val Pro Tyr Ile Tyr Met Gly Cys Lys Phe Tyr Asp Phe
                130                 135                 140

Phe Gly Gly Ser Gln Asn Leu Lys Lys Ser Tyr Leu Leu Ser Lys Ser
145                 150                 155                 160

Ala Thr Val Glu Lys Ala Pro Met Leu Thr Thr Asp Asn Leu Lys Ala
                165                 170                 175

Ser Leu Val Tyr His Asp Gly Ser Phe Asn Asp Ser Arg Leu Asn Ala
```

```
                    180              185              190
Thr Leu Ala Ile Thr Gly Val Glu Asn Gly Ala Thr Val Leu Ile Tyr
            195              200              205
Val Glu Val Gln Lys Leu Ile Lys Asp Pro Thr Ser Gly Lys Val Ile
210              215              220
Gly Ala Glu Ala Arg Asp Val Glu Thr Asn Glu Leu Val Arg Ile Asn
225              230              235              240
Ala Lys Cys Val Val Asn Ala Thr Gly Pro Tyr Ser Asp Ala Ile Leu
                245              250              255
Gln Met Asp Arg Asn Pro Ser Gly Leu Pro Asp Ser Pro Leu Asn Asp
            260              265              270
Asn Ser Lys Ile Lys Ser Thr Phe Asn Gln Ile Ser Val Met Asp Pro
        275              280              285
Lys Met Val Ile Pro Ser Ile Gly Val His Ile Val Leu Pro Ser Phe
    290              295              300
Tyr Ser Pro Lys Asp Met Gly Leu Leu Asp Val Arg Thr Ser Asp Gly
305              310              315              320
Arg Val Met Phe Phe Leu Pro Trp Gln Gly Lys Val Leu Ala Gly Thr
                325              330              335
Thr Asp Ile Pro Leu Lys Gln Val Pro Glu Asn Pro Met Pro Thr Glu
            340              345              350
Ala Asp Ile Gln Asp Ile Leu Lys Glu Leu Gln His Tyr Ile Glu Phe
        355              360              365
Pro Val Lys Arg Glu Asp Val Leu Ser Ala Trp Ala Gly Val Arg Pro
    370              375              380
Leu Val Arg Asp Pro Arg Thr Ile Pro Ala Asp Gly Lys Lys Gly Ser
385              390              395              400
Ala Thr Gln Gly Val Val Arg Ser His Phe Leu Phe Thr Ser Asp Asn
                405              410              415
Gly Leu Ile Thr Ile Ala Gly Gly Lys Trp Thr Thr Tyr Arg Gln Met
            420              425              430
Ala Glu Glu Thr Val Asp Lys Val Val Glu Val Gly Gly Phe His Asn
        435              440              445
Leu Lys Pro Cys His Thr Arg Asp Ile Lys Leu Ala Gly Ala Glu Glu
    450              455              460
Trp Thr Gln Asn Tyr Val Ala Leu Leu Ala Gln Asn Tyr His Leu Ser
465              470              475              480
Ser Lys Met Ser Asn Tyr Leu Val Gln Asn Tyr Gly Thr Arg Ser Ser
                485              490              495
Ile Ile Cys Glu Phe Phe Lys Glu Ser Met Glu Asn Lys Leu Pro Leu
            500              505              510
Ser Leu Ala Asp Lys Glu Asn Asn Val Ile Tyr Ser Ser Glu Glu Asn
        515              520              525
Asn Leu Val Asn Phe Asp Thr Phe Arg Tyr Pro Phe Thr Ile Gly Glu
    530              535              540
Leu Lys Tyr Ser Met Gln Tyr Glu Tyr Cys Arg Thr Pro Leu Asp Phe
545              550              555              560
Leu Leu Arg Arg Thr Arg Phe Ala Phe Leu Asp Ala Lys Glu Ala Leu
                565              570              575
Asn Ala Val His Ala Thr Val Lys Val Met Gly Asp Glu Phe Asn Trp
            580              585              590
Ser Glu Lys Lys Arg Gln Trp Glu Leu Glu Lys Thr Val Asn Phe Ile
        595              600              605
```

Gln Gly Arg Phe Gly Val
          610

(2) INFORMATION FOR SEQ ID NO: 10:

(i) SEQUENCE CHARACTERISTICS:
       (A) LENGTH: 339 amino acids
       (B) TYPE: amino acid
       (C) STRANDEDNESS: unknown
       (D) TOPOLOGY: unknown (ii) MOLECULE TYPE: protein (xi) SEQUENCE DESCRIPTION: SEQ ID NO: 10:

Met Asn Gln Arg Asn Ala Ser Met Thr Val Ile Gly Ala Gly Ser Tyr
1               5                   10                  15

Gly Thr Ala Leu Ala Ile Thr Leu Ala Arg Asn Gly His Glu Val Val
            20                  25                  30

Leu Trp Gly His Asp Pro Glu His Ile Ala Thr Leu Glu Arg Asp Arg
        35                  40                  45

Cys Asn Ala Ala Phe Leu Pro Asp Val Pro Phe Pro Asp Thr Leu His
    50                  55                  60

Leu Glu Ser Asp Leu Ala Thr Ala Leu Ala Ser Arg Asn Ile Leu
65                  70                  75                  80

Val Val Val Pro Ser His Val Phe Gly Glu Val Leu Arg Gln Ile Lys
                85                  90                  95

Pro Leu Met Arg Pro Asp Ala Arg Leu Val Trp Ala Thr Lys Gly Leu
            100                 105                 110

Glu Ala Glu Thr Gly Arg Leu Leu Gln Asp Val Ala Arg Glu Ala Leu
        115                 120                 125

Gly Asp Gln Ile Pro Leu Ala Val Ile Ser Gly Pro Thr Phe Ala Lys
    130                 135                 140

Glu Leu Ala Ala Gly Leu Pro Thr Ala Ile Ser Leu Ala Ser Thr Asp
145                 150                 155                 160

Gln Thr Phe Ala Asp Asp Leu Gln Gln Leu Leu His Cys Gly Lys Ser
                165                 170                 175

Phe Arg Val Tyr Ser Asn Pro Asp Phe Ile Gly Val Gln Leu Gly Gly
            180                 185                 190

Ala Val Lys Asn Val Ile Ala Ile Gly Ala Gly Met Ser Asp Gly Ile
        195                 200                 205

Gly Phe Gly Ala Asn Ala Arg Thr Ala Leu Ile Thr Arg Gly Leu Ala
    210                 215                 220

Glu Met Ser Arg Leu Gly Ala Ala Leu Gly Ala Asp Pro Ala Thr Phe
225                 230                 235                 240

Met Gly Met Ala Gly Leu Gly Asp Leu Val Leu Thr Cys Thr Asp Asn
                245                 250                 255

Gln Ser Arg Asn Arg Arg Phe Gly Met Met Leu Gly Gln Gly Met Asp
            260                 265                 270

Val Gln Ser Ala Gln Glu Lys Ile Gly Gln Val Val Glu Gly Tyr Arg
        275                 280                 285

Asn Thr Lys Glu Val Arg Glu Leu Ala His Arg Phe Gly Val Glu Met
    290                 295                 300

Pro Ile Thr Glu Glu Ile Tyr Gln Val Leu Tyr Cys Gly Lys Asn Ala
305                 310                 315                 320

Arg Glu Ala Ala Leu Thr Leu Leu Gly Arg Ala Arg Lys Asp Glu Arg
                325                 330                 335

Ser Ser His (2) INFORMATION FOR SEQ ID NO: 11:

(i) SEQUENCE CHARACTERISTICS:
       (A) LENGTH: 501 amino acids
       (B) TYPE: amino acid
       (C) STRANDEDNESS: unknown
       (D) TOPOLOGY: unknown (ii) MOLECULE TYPE: protein (xi) SEQUENCE DESCRIPTION: SEQ ID NO: 11:

```
Met Glu Thr Lys Asp Leu Ile Val Ile Gly Gly Ile Asn Gly Ala
1               5                   10                  15

Gly Ile Ala Ala Asp Ala Ala Gly Arg Gly Leu Ser Val Leu Met Leu
            20                  25                  30

Glu Ala Gln Asp Leu Ala Cys Ala Thr Ser Ser Ala Ser Ser Lys Leu
            35                  40                  45

Ile His Gly Gly Leu Arg Tyr Leu Glu His Tyr Glu Phe Arg Leu Val
50                  55                  60

Ser Glu Ala Leu Ala Glu Arg Glu Val Leu Leu Lys Met Ala Pro His
65                  70                  75                  80

Ile Ala Phe Pro Met Arg Phe Arg Leu Pro His Arg Pro His Leu Arg
                85                  90                  95

Pro Ala Trp Met Ile Arg Ile Gly Leu Phe Met Tyr Asp His Leu Gly
                100                 105                 110

Lys Arg Thr Ser Leu Pro Gly Ser Thr Gly Leu Arg Phe Gly Ala Asn
                115                 120                 125

Ser Val Leu Lys Pro Glu Ile Lys Arg Gly Phe Glu Tyr Ser Asp Cys
130                 135                 140

Trp Val Asp Asp Ala Arg Leu Val Leu Ala Asn Ala Gln Met Val Val
145                 150                 155                 160

Arg Lys Gly Gly Glu Val Leu Thr Arg Thr Arg Ala Thr Ser Ala Arg
                165                 170                 175

Arg Glu Asn Gly Leu Trp Ile Val Glu Ala Glu Asp Ile Asp Thr Gly
                180                 185                 190

Lys Lys Tyr Ser Trp Gln Ala Arg Gly Leu Val Asn Ala Thr Gly Pro
                195                 200                 205

Trp Val Lys Gln Phe Phe Asp Asp Gly Met His Leu Pro Ser Pro Tyr
                210                 215                 220

Gly Ile Arg Leu Ile Lys Gly Ser His Ile Val Val Pro Arg Val His
225                 230                 235                 240

Thr Gln Lys Gln Ala Tyr Ile Leu Gln Asn Glu Asp Lys Arg Ile Val
                245                 250                 255

Phe Val Ile Pro Trp Met Asp Glu Phe Ser Ile Ile Gly Thr Thr Asp
                260                 265                 270

Val Glu Tyr Lys Gly Asp Pro Lys Ala Val Lys Ile Glu Glu Ser Glu
                275                 280                 285

Ile Asn Tyr Leu Leu Asn Val Tyr Asn Thr His Phe Lys Lys Gln Leu
                290                 295                 300

Ser Arg Asp Asp Ile Val Trp Thr Tyr Ser Gly Val Arg Pro Leu Cys
305                 310                 315                 320

Asp Asp Glu Ser Asp Ser Pro Gln Ala Ile Thr Arg Asp Tyr Thr Leu
                325                 330                 335
```

```
Asp Ile His Asp Glu Asn Gly Lys Ala Pro Leu Leu Ser Val Phe Gly
            340                 345                 350

Gly Lys Leu Thr Thr Tyr Arg Lys Leu Ala Glu His Ala Leu Glu Lys
            355                 360                 365

Leu Thr Pro Tyr Tyr Gln Gly Ile Gly Pro Ala Trp Thr Lys Glu Ser
            370                 375                 380

Val Leu Pro Gly Gly Ala Ile Glu Gly Asp Arg Asp Tyr Ala Ala
385                 390                 395                 400

Arg Leu Arg Arg Arg Tyr Pro Phe Leu Thr Glu Ser Leu Ala Arg His
            405                 410                 415

Tyr Ala Arg Thr Tyr Gly Ser Asn Ser Glu Leu Leu Gly Asn Ala
            420                 425                 430

Gly Thr Val Ser Asp Leu Gly Glu Asp Phe Gly His Glu Phe Tyr Glu
            435                 440                 445

Ala Glu Leu Lys Tyr Leu Val Asp His Glu Trp Val Arg Arg Ala Asp
            450                 455                 460

Asp Ala Leu Trp Arg Arg Thr Lys Gln Gly Met Trp Leu Asn Ala Asp
465                 470                 475                 480

Gln Gln Ser Arg Val Ser Gln Trp Leu Val Glu Tyr Thr Gln Gln Arg
            485                 490                 495

Leu Ser Leu Ala Ser
            500

(2) INFORMATION FOR SEQ ID NO: 12:

(i) SEQUENCE CHARACTERISTICS:
        (A) LENGTH: 542 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 12:

Met Lys Thr Arg Asp Ser Gln Ser Ser Asp Val Ile Ile Gly Gly
1               5                   10                  15

Gly Ala Thr Gly Ala Gly Ile Ala Arg Asp Cys Ala Leu Arg Gly Leu
            20                  25                  30

Arg Val Ile Leu Val Glu Arg His Asp Ile Ala Thr Gly Ala Thr Gly
            35                  40                  45

Arg Asn His Gly Leu Leu His Ser Gly Ala Arg Tyr Ala Val Thr Asp
            50                  55                  60

Ala Glu Ser Ala Arg Glu Cys Ile Ser Glu Asn Gln Ile Leu Lys Arg
65                  70                  75                  80

Ile Ala Arg His Cys Val Glu Pro Thr Asn Gly Leu Phe Ile Thr Leu
            85                  90                  95

Pro Glu Asp Asp Leu Ser Phe Gln Ala Thr Phe Ile Arg Ala Cys Glu
            100                 105                 110

Glu Ala Gly Ile Ser Ala Glu Ala Ile Asp Pro Gln Gln Ala Arg Ile
            115                 120                 125

Ile Glu Pro Ala Val Asn Pro Ala Leu Ile Gly Ala Val Lys Val Pro
            130                 135                 140

Asp Gly Thr Val Asp Pro Phe Arg Leu Thr Ala Ala Asn Met Leu Asp
145                 150                 155                 160

Ala Lys Glu His Gly Ala Val Ile Leu Thr Ala His Glu Val Thr Gly
            165                 170                 175
```

```
Leu Ile Arg Glu Gly Ala Thr Val Cys Gly Val Arg Val Arg Asn His
            180                 185                 190

Leu Thr Gly Glu Thr Gln Ala Leu His Ala Pro Val Val Asn Ala
            195                 200                 205

Ala Gly Ile Trp Gly Gln His Ile Ala Glu Tyr Ala Asp Leu Arg Ile
            210                 215                 220

Arg Met Phe Pro Ala Lys Gly Ser Leu Leu Ile Met Asp His Arg Ile
225                 230                 235                 240

Asn Gln His Val Ile Asn Arg Cys Arg Lys Pro Ser Asp Ala Asp Ile
                245                 250                 255

Leu Val Pro Gly Asp Thr Ile Ser Leu Ile Gly Thr Thr Ser Leu Arg
            260                 265                 270

Ile Asp Tyr Asn Glu Ile Asp Asn Arg Val Thr Ala Glu Glu Val
            275                 280                 285

Asp Ile Leu Leu Arg Glu Gly Glu Lys Leu Ala Pro Val Met Ala Lys
            290                 295                 300

Thr Arg Ile Leu Arg Ala Tyr Ser Gly Val Arg Pro Leu Val Ala Ser
305                 310                 315                 320

Asp Asp Asp Pro Ser Gly Arg Asn Leu Ser Arg Gly Ile Val Leu Leu
                325                 330                 335

Asp His Ala Glu Arg Asp Gly Leu Asp Gly Phe Ile Thr Ile Thr Gly
            340                 345                 350

Gly Lys Leu Met Thr Tyr Arg Leu Met Ala Glu Trp Ala Thr Asp Ala
            355                 360                 365

Val Cys Arg Lys Leu Gly Asn Thr Arg Pro Cys Thr Thr Ala Asp Leu
370                 375                 380

Ala Leu Pro Gly Ser Gln Glu Pro Ala Glu Val Thr Leu Arg Lys Val
385                 390                 395                 400

Ile Ser Leu Pro Ala Pro Leu Arg Gly Ser Ala Val Tyr Arg His Gly
                405                 410                 415

Asp Arg Thr Pro Ala Trp Leu Ser Glu Gly Arg Leu His Arg Ser Leu
            420                 425                 430

Val Cys Glu Cys Glu Ala Val Thr Ala Gly Glu Val Gln Tyr Ala Val
            435                 440                 445

Glu Asn Leu Asn Val Asn Ser Leu Leu Asp Leu Arg Arg Arg Thr Arg
            450                 455                 460

Val Gly Met Gly Thr Cys Gln Gly Glu Leu Cys Ala Cys Arg Ala Ala
465                 470                 475                 480

Gly Leu Leu Gln Arg Phe Asn Val Thr Thr Ser Ala Gln Ser Ile Glu
                485                 490                 495

Gln Leu Ser Thr Phe Leu Asn Glu Arg Trp Lys Gly Val Gln Pro Ile
            500                 505                 510

Ala Trp Gly Asp Ala Leu Arg Glu Ser Glu Phe Thr Arg Trp Val Tyr
            515                 520                 525

Gln Gly Leu Cys Gly Leu Glu Lys Glu Gln Lys Asp Ala Leu
            530                 535                 540

(2) INFORMATION FOR SEQ ID NO: 13:

(i) SEQUENCE CHARACTERISTICS:
        (A) LENGTH: 250 amino acids
        (B) TYPE: amino acid
        (C) STRANDEDNESS: unknown
        (D) TOPOLOGY: unknown (ii) MOLECULE TYPE: protein
```

(xi) SEQUENCE DESCRIPTION: SEQ ID NO: 13:

Met Gly Leu Thr Thr Lys Pro Leu Ser Leu Lys Val Asn Ala Ala Leu
1               5                   10                  15

Phe Asp Val Asp Gly Thr Ile Ile Ile Ser Gln Pro Ala Ile Ala Ala
                20                  25                  30

Phe Trp Arg Asp Phe Gly Lys Asp Lys Pro Tyr Phe Asp Ala Glu His
            35                  40                  45

Val Ile Gln Val Ser His Gly Trp Arg Thr Phe Asp Ala Ile Ala Lys
        50                  55                  60

Phe Ala Pro Asp Phe Ala Asn Glu Glu Tyr Val Asn Lys Leu Glu Ala
65                  70                  75                  80

Glu Ile Pro Val Lys Tyr Gly Glu Lys Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Gln Lys Trp Phe Glu His
        115                 120                 125

Leu Gly Ile Arg Arg Pro Lys Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Ile Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250

(2) INFORMATION FOR SEQ ID NO: 14:

(i) SEQUENCE CHARACTERISTICS:
        (A) LENGTH: 271 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 14:

Met Lys Arg Phe Asn Val Leu Lys Tyr Ile Arg Thr Thr Lys Ala Asn
1               5                   10                  15

Ile Gln Thr Ile Ala Met Pro Leu Thr Thr Lys Pro Leu Ser Leu Lys
                20                  25                  30

Ile Asn Ala Ala Leu Phe Asp Val Asp Gly Thr Ile Ile Ile Ser Gln
            35                  40                  45

Pro Ala Ile Ala Ala Phe Trp Arg Asp Phe Gly Lys Asp Lys Pro Tyr
        50                  55                  60

Phe Asp Ala Glu His Val Ile His Ile Ser His Gly Trp Arg Thr Tyr
65                  70                  75                  80

```
Asp Ala Ile Ala Lys Phe Ala Pro Asp Phe Ala Asp Glu Glu Tyr Val
                85                  90                  95

Asn Lys Leu Glu Gly Glu Ile Pro Glu Lys Tyr Gly Glu His Ser Ile
            100                 105                 110

Glu Val Pro Gly Ala Val Lys Leu Cys Asn Ala Leu Asn Ala Leu Pro
        115                 120                 125

Lys Glu Lys Trp Ala Val Ala Thr Ser Gly Thr Arg Asp Met Ala Lys
    130                 135                 140

Lys Trp Phe Asp Ile Leu Lys Ile Lys Arg Pro Glu Tyr Phe Ile Thr
145                 150                 155                 160

Ala Asn Asp Val Lys Gln Gly Lys Pro His Pro Glu Pro Tyr Leu Lys
                165                 170                 175

Gly Arg Asn Gly Leu Gly Phe Pro Ile Asn Glu Gln Asp Pro Ser Lys
            180                 185                 190

Ser Lys Val Val Phe Glu Asp Ala Pro Ala Gly Ile Ala Ala Gly
        195                 200                 205

Lys Ala Ala Gly Cys Lys Ile Val Gly Ile Ala Thr Thr Phe Asp Leu
    210                 215                 220

Asp Phe Leu Lys Glu Lys Gly Cys Asp Ile Ile Val Lys Asn His Glu
225                 230                 235                 240

Ser Ile Arg Val Gly Glu Tyr Asn Ala Glu Thr Asp Glu Val Glu Leu
                245                 250                 255

Ile Phe Asp Asp Tyr Leu Tyr Ala Lys Asp Leu Leu Lys Trp
            260                 265                 270

(2) INFORMATION FOR SEQ ID NO: 15:

(i) SEQUENCE CHARACTERISTICS:
        (A) LENGTH: 709 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 15:

Met Phe Pro Ser Leu Phe Arg Leu Val Val Phe Ser Lys Arg Tyr Ile
1               5                   10                  15

Phe Arg Ser Ser Gln Arg Leu Tyr Thr Ser Leu Lys Gln Glu Gln Ser
            20                  25                  30

Arg Met Ser Lys Ile Met Glu Asp Leu Arg Ser Asp Tyr Val Pro Leu
        35                  40                  45

Ile Ala Ser Ile Asp Val Gly Thr Thr Ser Ser Arg Cys Ile Leu Phe
    50                  55                  60

Asn Arg Trp Gly Gln Asp Val Ser Lys His Gln Ile Glu Tyr Ser Thr
65                  70                  75                  80

Ser Ala Ser Lys Gly Lys Ile Gly Val Ser Gly Leu Arg Arg Pro Ser
                85                  90                  95

Thr Ala Pro Ala Arg Glu Thr Pro Asn Ala Gly Asp Ile Lys Thr Ser
            100                 105                 110

Gly Lys Pro Ile Phe Ser Ala Glu Gly Tyr Ala Ile Gln Glu Thr Lys
        115                 120                 125

Phe Leu Lys Ile Glu Glu Leu Asp Leu Asp Phe His Asn Glu Pro Thr
    130                 135                 140

Leu Lys Phe Pro Lys Pro Gly Trp Val Glu Cys His Pro Gln Lys Leu
145                 150                 155                 160
```

```
Leu Val Asn Val Val Gln Cys Leu Ala Ser Ser Leu Ser Leu Gln
            165                 170                 175

Thr Ile Asn Ser Glu Arg Val Ala Asn Gly Leu Pro Pro Tyr Lys Val
        180                 185                 190

Ile Cys Met Gly Ile Ala Asn Met Arg Glu Thr Thr Ile Leu Trp Ser
            195                 200                 205

Arg Arg Thr Gly Lys Pro Ile Val Asn Tyr Gly Ile Val Trp Asn Asp
    210                 215                 220

Thr Arg Thr Ile Lys Ile Val Arg Asp Lys Trp Gln Asn Thr Ser Val
225                 230                 235                 240

Asp Arg Gln Leu Gln Leu Arg Gln Lys Thr Gly Leu Pro Leu Leu Ser
            245                 250                 255

Thr Tyr Phe Ser Cys Ser Lys Leu Arg Trp Phe Leu Asp Asn Glu Pro
            260                 265                 270

Leu Cys Thr Lys Ala Tyr Glu Glu Asn Asp Leu Met Phe Gly Thr Val
            275                 280                 285

Asp Thr Trp Leu Ile Tyr Gln Leu Thr Lys Gln Lys Ala Phe Val Ser
    290                 295                 300

Asp Val Thr Asn Ala Ser Arg Thr Gly Phe Met Asn Leu Ser Thr Leu
305                 310                 315                 320

Lys Tyr Asp Asn Glu Leu Leu Glu Phe Trp Gly Ile Asp Lys Asn Leu
            325                 330                 335

Ile His Met Pro Glu Ile Val Ser Ser Gln Tyr Tyr Gly Asp Phe
            340                 345                 350

Gly Ile Pro Asp Trp Ile Met Glu Lys Leu His Asp Ser Pro Lys Thr
            355                 360                 365

Val Leu Arg Asp Leu Val Lys Arg Asn Leu Pro Ile Gln Gly Cys Leu
    370                 375                 380

Gly Asp Gln Ser Ala Ser Met Val Gly Gln Leu Ala Tyr Lys Pro Gly
385                 390                 395                 400

Ala Ala Lys Cys Thr Tyr Gly Thr Gly Cys Phe Leu Leu Tyr Asn Thr
            405                 410                 415

Gly Thr Lys Lys Leu Ile Ser Gln His Gly Ala Leu Thr Thr Leu Ala
            420                 425                 430

Phe Trp Phe Pro His Leu Gln Glu Tyr Gly Gly Gln Lys Pro Glu Leu
            435                 440                 445

Ser Lys Pro His Phe Ala Leu Glu Gly Ser Val Ala Val Ala Gly Ala
    450                 455                 460

Val Val Gln Trp Leu Arg Asp Asn Leu Arg Leu Ile Asp Lys Ser Glu
465                 470                 475                 480

Asp Val Gly Pro Ile Ala Ser Thr Val Pro Asp Ser Gly Val Val
            485                 490                 495

Phe Val Pro Ala Phe Ser Gly Leu Phe Ala Pro Tyr Trp Asp Pro Asp
            500                 505                 510

Ala Arg Ala Thr Ile Met Gly Met Ser Gln Phe Thr Thr Ala Ser His
            515                 520                 525

Ile Ala Arg Ala Ala Val Glu Gly Val Cys Phe Gln Ala Arg Ala Ile
    530                 535                 540

Leu Lys Ala Met Ser Ser Asp Ala Phe Gly Glu Gly Ser Lys Asp Arg
545                 550                 555                 560

Asp Phe Leu Glu Glu Ile Ser Asp Val Thr Tyr Glu Lys Ser Pro Leu
            565                 570                 575

Ser Val Leu Ala Val Asp Gly Gly Met Ser Arg Ser Asn Glu Val Met
```

-continued

```
                580                 585                 590
Gln Ile Gln Ala Asp Ile Leu Gly Pro Cys Val Lys Val Arg Arg Ser
            595                 600                 605
Pro Thr Ala Glu Cys Thr Ala Leu Gly Ala Ala Ile Ala Ala Asn Met
        610                 615                 620
Ala Phe Lys Asp Val Asn Glu Arg Pro Leu Trp Lys Asp Leu His Asp
625                 630                 635                 640
Val Lys Lys Trp Val Phe Tyr Asn Gly Met Glu Lys Asn Glu Gln Ile
                645                 650                 655
Ser Pro Glu Ala His Pro Asn Leu Lys Ile Phe Arg Ser Glu Ser Asp
            660                 665                 670
Asp Ala Glu Arg Arg Lys His Trp Lys Tyr Trp Glu Val Ala Val Glu
        675                 680                 685
Arg Ser Lys Gly Trp Leu Lys Asp Ile Glu Gly Glu His Glu Gln Val
    690                 695                 700
Leu Glu Asn Phe Gln
705
```

(2) INFORMATION FOR SEQ ID NO: 16:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

GCGCGGATCC AGGAGTCTAG AATTATGGGA TTGACTACTA AACCTCTATC T        51

(2) INFORMATION FOR SEQ ID NO: 17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GATACGCCCG GGTTACCATT TCAACAGATC GTCCTT        36

(2) INFORMATION FOR SEQ ID NO: 18:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

TTGATAATAT AACCATGGCT GCTGCTGCTG ATAG        34

(2) INFORMATION FOR SEQ ID NO: 19:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

GTATGATATG TTATCTTGGA TCCAATAAAT CTAATCTTC                      39

(2) INFORMATION FOR SEQ ID NO: 20:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 20:

CATGACTAGT AAGGAGGACA ATTC                                     24

(2) INFORMATION FOR SEQ ID NO: 21:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 21:

CATGGAATTG TCCTCCTTAC TAGT                                     24

(2) INFORMATION FOR SEQ ID NO: 22:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 22:

CTAGTAAGGA GGACAATTC                                           19

(2) INFORMATION FOR SEQ ID NO: 23:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 23:

CATGGAATTG TCCTCCTTA                                           19

(2) INFORMATION FOR SEQ ID NO: 24:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

-continued (iii) HYPOTHETICAL: NO (iv) ANTI-SENSE: NO (xi) SEQUENCE DESCRIPTION: SEQ ID NO: 24:

GATCCAGGAA ACAGA                                                           15

(2) INFORMATION FOR SEQ ID NO: 25:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (xi) SEQUENCE DESCRIPTION: SEQ ID NO: 25:

CTAGTCTGTT TCCTG                                                           15